US009018367B2

(12) United States Patent
Widen et al.

(10) Patent No.: US 9,018,367 B2
(45) Date of Patent: Apr. 28, 2015

(54) SINGLE STRANDED DNA APTAMERS BINDING NF-κB/RELA

(75) Inventors: Steven G. Widen, Galveston, TX (US);
Thomas G. Wood, Houston, TX (US);
Allan R. Brasier, Galveston, TX (US);
Yingxin Zhao, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 53 days.

(21) Appl. No.: 13/445,558

(22) Filed: Apr. 12, 2012

(65) Prior Publication Data

US 2012/0263651 A1    Oct. 18, 2012

Related U.S. Application Data

(60) Provisional application No. 61/474,674, filed on Apr. 12, 2011.

(51) Int. Cl.
| | | |
|---|---|---|
| *C07H 21/00* | (2006.01) | |
| *A61K 49/00* | (2006.01) | |
| *A61K 47/48* | (2006.01) | |
| *A61K 31/7088* | (2006.01) | |
| *C12N 15/115* | (2010.01) | |

(52) U.S. Cl.
CPC ....... *A61K 49/0002* (2013.01); *A61K 47/48092* (2013.01); *A61K 31/7088* (2013.01); *C12N 15/115* (2013.01); *C12N 2310/16* (2013.01); *C12N 2310/3517* (2013.01)

(58) Field of Classification Search
None
See application file for complete search history.

(56) References Cited

U.S. PATENT DOCUMENTS

| | | | |
|---|---|---|---|
| 6,867,289 | B1 | 3/2005 | Gorenstein et al. |
| 7,309,786 | B2 | 12/2007 | Zhang et al. |
| 2008/0261225 | A1 | 10/2008 | Ahn et al. |

OTHER PUBLICATIONS

Addona, Terri A., et al., "Multi-Site Assessment of the Precision and Reproducibility of Multiple Reaction Monitoring-Based Measurements of Proteins in Plasma," Nat. Biotechnol. 27(7), Jul. 2009, pp. 633-641.
Akagi, Tsuyoshi, et al., Refractory Nature of Normal Human Diploid Fibroblasts with Respect to Oncogene-Mediated Transformation, PNAS, Nov. 11, 2003, vol. 100, No. 23, pp. 13567-13572.
Akira, Shizuo, et al., "Pathogen Recognition and Innate Immunity," Cell, Feb. 24, 2006, 124, pp. 783-801.
Barnes, Peter J., et al., "Nuclear Factor-KB—A Pivotal Transcription Factor in Chronic Inflammatory Diseases," The New England Journal of Medicine, Apr. 10, 1997, vol. 336, No. 15, pp. 1066-1071.
Bassett, Suzanne E., et al., "Combinatorial Selection and Edited Combinatorial Selection of Phosphorothioate Aptamers Targeting Human Nuclear Factor-KB RelA/p50 and RelA/RelA," Biochemistry, 11 pages.
Beg, Amer A., et al., "The IKB Proteins: Multifunctional Regulators of Rel/NF-KB Transcription Factors," Genes & Development, 1993, 7:2064-2070.
Berezovski, Maxim V., et al., "Aptamer-Facilitated Biomarker Discovery (AptaBID)," J. Am. Chem. Soc., 2008 130:9137-9143.
Bosisio, Daniela, et al., "A Hyper-Dynamic Equilibrium Between Promoter-Bound and Nucleoplasmic Dimers Controls NF-KB-Dependent Gene Activity," The EMBO Journal, 2006, vol. 25, No. 4, pp. 798-810.
Bouwmeester, Tewis, et al., "A Physical and Functional Map of the Human TNF-/NK-KB Signal Transduction Pathway," Nature Cell Biology, Feb. 2004, vol. 6, No. 2, pp. 97-106.
Brand, Korbinian, et al., "Activated Transcription Factor Nuclear Factor-Kappa B is Present in the Atherosclerotic Lesion," J. Clin. Invest., Apr. 1996, vol. 97, No. 7, pp. 1715-1722.
Brasier, Allan R., et al., "Chapter 32: Vascular Inflammation as a Cardiovascular Risk Factor," Contemporary Cardiology: Principles of Molecular Cardiology, Apr. 1, 2005, pp. 577-604.
Brasier, Allan R., "Chapter 9: The Nuclear Factor-KB Signaling Network: Insights from Systems Approaches," Cellular Signaling and Innate Immune Responses to RNA Virus Infections, 2009, pp. 119-136.
Brasier, Allan R., et al., "Vascular Inflammation and the Renin-Angiotensin System," Arteriosclerosis, Thrombosis, and Vascular Biology, Journal of the American Heart Association, May 9, 2002, pp. 1256-1266.
Brasier, Allan R., "The Nuclear Factor-KB-Interleukin-6 Signalling Pathway Mediating Vascular Inflammation," Cardiovascular Research, (2010), 86:211-218.
Chen, Yong-Qing, et al., "A Novel DNA Recognition Mode by the NF-KB p65 Homodimer," Nature Structural Biology, vol. 5, No. 1, Jan. 1998, pp. 67-73.
Chen, Lin-Feng, et al., "NF-KB RelA Phosphorylation Regulates RElA Acetylation," Molecular and Cellular Biology, Sep. 2005, pp. 7966-7975.
Cui, Ruwen, et al., "RhoA Mediates Angiotensin II-Induced Phospho-Ser536 Nuclear Factor KB/RelA Subunit Exchange on the Interleukin-6 Promoter in VSMC's," Circ. Res., 2006, 99:723-730.

(Continued)

*Primary Examiner* — Jennifer McDonald
(74) *Attorney, Agent, or Firm* — Edwin S. Flores; Chalker Flores, LLP

(57) ABSTRACT

DNA aptamers are high affinity ligands selected by genetic enrichment techniques to bind to specific protein targets. Because these represent chemically stable and reproducible molecules, they have application as affinity reagents and/or therapeutic drugs to affect the target protein's actions. NF-kB is an important mediator of the innate immune response and mediator of tissue inflammation. Although RNA and double stranded DNA aptamers have been identified to bind to the NF-kB family of proteins, the present invention represents the first identification of single stranded DNA aptamers that recognize NFkB RelA. The aptamers disclosed herein bind to several distinct regions of RelA and may be useful to antagonize the DNA binding of RelA as an inhibitor of cellular inflammation, visualize the location or amount of RelA in tissues from pathological conditions, or to quantitatively measure the activated state of RelA by affinity binding.

12 Claims, 14 Drawing Sheets

(56) References Cited

OTHER PUBLICATIONS

Delhase, Mireille, et al., "Positive and Negative Regulation of IKB Kinase Activity Through IKKB Subunit Phosphorylation," Science, (1999), 284:309, pp. 309-313.
Dror, Rinat, et al., "Characterizing the Involvement of the Nuclear Factor-Kappa B (NFkB) Transcription Factor in Uveal Melanoma," IOVS, Apr. 2010, vol. 51, No. 4, pp. 1811-1816.
Ea, Chee-Kwee, et al., "Activation of IKK by TNFa Requires Site-Specific Ubiquitination of RIP1 and Polyubiquitin Binding by NEMO," Molecular Cell, Apr. 21, 2006, 22:245-257.
Ellington, Andrew D., et al., "In Vitro Selection of RNA Molecules that Bind Specific Ligands," Nature, Aug. 30, 1990, vol. 346, pp. 818-822.
Forbus, Jeffery, et al., "Functional Analysis of the Nuclear Proteome of Human A549 Alveolar Epithelial Cells by HPLC-High Resolution 2-D Gel Electrophoresis," Proteomics, (2006), 6:2656-2672.
Garofalo, Roberto, et al., "Transcriptional Activation of the Interleukin-8 Gene by Respiratory Syncytial Virus Infection in Alveolar Epithelial Cells: Nuclear Translocation of the RelA Transcription Factor as a Mechanism Producing Airway Mucosal Inflammation," Journal of Virology, Dec. 1996, vol. 70, No. 12, pp. 8773-8781.
Green, J. Mark, "A Practical Guide to Analytical Method Validation," Analytical Chemistry News & Features, May 1, 1996, pp. 305-309.
Greten, Florian R., et al., "IKKB Links Inflammation and Tumorigenesis in a Mouse Model of Colitis-Associated Cancer," Cell, Aug. 6, 2004, vol. 119, pp. 285-296.
Han, Youqi, et al., "Tumor Necrosis Factor-a-Inducible IKBA Proteolysis Mediated by Cytosolic m-Calpain," The Journal of Biological Chemistry, Jan. 8, 1999, vol. 274, No. 2, pp. 787-794.
Hoffmann, Alexander, et al., "The IKB-NF Signaling Module: Temporal Control and Selective Gene Activation," Science, (2002), 298:1241-1245.
Hou, Tieying, et al., "The Functional Role of an Interleukin 6-Inducible CDK9-STAT3 Complex in Human y-Fibrinogen Gene Expression," The Journal of Biological Chemistry, Dec. 21, 2007, vol. 282, No. 51, pp. 37091-37102.
Hsu, Hailing, et al., "TNF-Dependent Recruitment of the Protein Kinase RIP to the TNF Receptor-1 Signaling Complex," Immunity, Apr. 1996, vol. 4, pp. 387-396.
Huang, De-Bin, et al., "Crystal Structure of NF-KB (p50)2 Complexed to a High-Affinity RNA Aptamer," PNAS, Aug. 5, 2003, vol. 100, No. 16, pp. 9268-9273.
Jacobs, Marc D., et al., "Structure of an IKBA/NF-KB Complex," Cell, Dec. 11, 1998, vol. 95, pp. 749-758.
Jamaluddin, Mohammad, et al., "The Major Component of IKBA Proteolysis Occurs Independently of the Proteasome Pathway in Respiratory Syncytial Virus-Infected Pulmonary Epithelial Cells," Journal of Virology, Jun. 1998, pp. 4849-4857.
Jamaluddin, Mohammad, et al., "TNF-A-Induced NF-KB-RelA Ser276 Phosphorylation and Enhanced Formation is Mediated by an ROS-Dependent PKAc Pathway," Cellular Signalling, (2007), 19:1419-1433.
Jamaluddin, Mohammad, et al., "Respiratory Syncytial Virus Infection Induces a Reactive Oxygen Species-MSK1-Phospho-Ser-276 RelA Pathway Required for Cytokine Expression," Journal of Virology, Oct. 2009, pp. 10605-10615.
Jamaluddin, Mohammad, et al., "Role of Peroxiredoxin 1 and Peroxiredoxin 4 in Protection of Respiratory Syncytial Virus-Induced Cysteinyl Oxidation of Nuclear Cytoskeletal Proteins," Journal of Virology, Sep. 2010, vol. 84, No. 18, pp. 9533-9545.
Kalita, Mridul K., et al., "Sources of Cell-to Cell Variability in Canonical Nuclear Factor-KB (NF-KB) Signaling Pathway Inferred from Single Cell Dynamic Images," The Journal of Biological Chemistry, Oct. 28, 2011, vol. 286, No. 43, pp. 37741-37757.
Karin, Michael, "The Beginning of the End: IKB Kinase (IKK) and NF-KB Activation," The Journal of Biological Chemistry, Sep. 24, 1999, vol. 274, No. 39, pp. 27339-27342.
Keshishian, Hasmik, et al., "Quantification of Cardiovascular Biomarkers in Patient Plasma by Targeted Mass Spectrometry and Stable Isotope Dilution," Molecular & Cellular Proteomics 8.10, (2009), pp. 2339-2349.
Kuhn, Eric, et al., "Developing Multiplexed Assays for Troponin I and Interleukin-33 in Plasma by Peptide Immunoaffinity Enrichment and Targeted Mass Spectrometry," Clinical Chemistry, (2009), 55:6, pp. 1108-1117.
Kuzyk, Michael A., et al., "Multiple Reaction Monitoring-Based, Multiplexed, Absolute Quantification of 45 Proteins in Human Plasma," Molecular & Cellular Proteomics 8.8, (2009), pp. 1860-1877.
Lange, Vinzenz, et al., "Selected Reaction Monitoring for Quantitative Proteomics: a Tutorial," Molecular Systems Biology, (2008), 14 pages.
Lipniacki, Tomasz, et al., "Mathematical Model of NF-KB Regulatory Module," Journal of Theoretical Biology, (2004), 228:195-215.
Liu, Ping, et al., "Expression of an IKKY Variant Determines IRF3 and Canonical NF-KB Pathway Utilization in ssRNA Virus Infection," PLOS, Nov. 2009, vol. 4, Issue 11, 15 pages.
Maniatis, Tom, "Catalysis by a Multiprotein IXB Kinase Complex," Science, Oct. 31, 1997, vol. 278, No. 5339, pp. 818-819.
Markham, Niicholas R., et al., "Software for Nucleic Acid Folding and Hybridization," Bioinformatics, vol. II: Structure, Function and Application, (2008), vol. 453, 29 pages.
Miceli, Robert M., et al., "Two-Stage Selection of Sequences from a Random Phage Display Library Delineates Both Core Residues and Permitted Structural Range within an Epitope," Journal of Immunological Methods, (1994), 167:279-287.
Nelson, D.E., et al., "Oscillations in NF-KB Signaling Control the Dynamics of Gene Expression," Science, Oct. 22, 2004, vol. 306, pp. 704-708.
Nowak, David E., et al., "Two-Step Cross-Linking Method for Identification of NF-KB Gene Network by Chromatin Immunoprecipitation," BioTechniques, Nov. 2005, 39:715-725.
Nowak, David E., et al., "RelA Ser276 Phosphorylation is Required for Activation of a Subset of NF-K B-Dependent Genes by Recruiting Cyclin-Dependent Kinase 9/Cyclin T1 Complexes," Mol. Cell. Biol., (2008), 28(11):3623-3637.

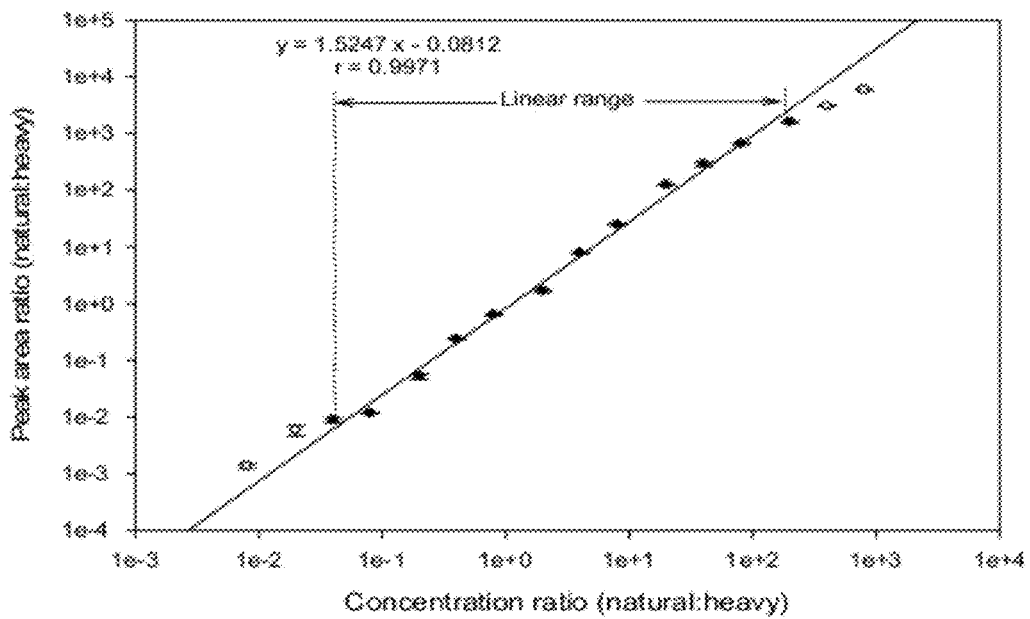
FIG. 9
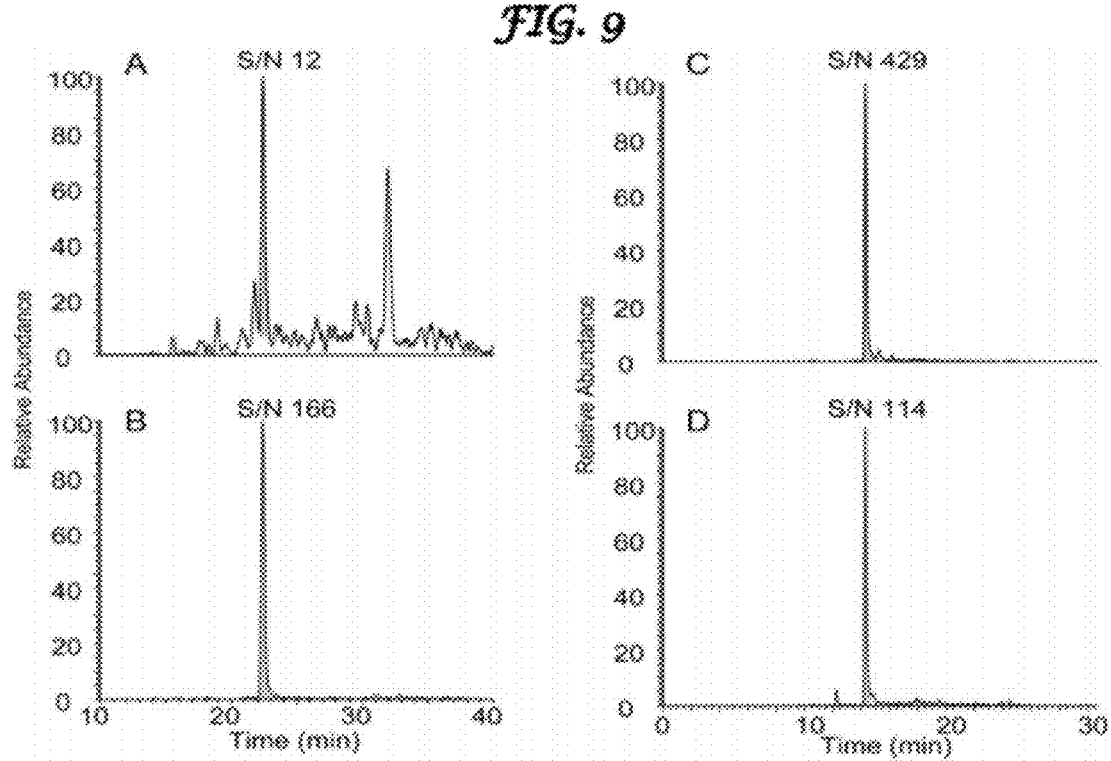
FIGS. 10A-D

SINGLE STRANDED DNA APTAMERS BINDING NF-κB/RELA

CROSS-REFERENCE TO RELATED APPLICATIONS

This application claims priority to U.S. Provisional Application Ser. No. 61/474,674, filed Apr. 12, 2011, the entire contents of which are incorporated herein by reference.

STATEMENT OF FEDERALLY FUNDED RESEARCH

This invention was made with U.S. Government support under Contract Nos. AI062885 and HHSN272200800048C awarded by the National Institutes of Health (NIH)/National Institute of Allergy and Infectious Diseases (NIAID). The government has certain rights in this invention.

TECHNICAL FIELD OF THE INVENTION

The present invention relates in general to the field of DNA aptamers, and more particularly, to the development of a single stranded DNA aptamer that recognizes and binds to activated NFkB RelA and its application in the quantification of activated RelA.

REFERENCE TO A SEQUENCE LISTING

The present application includes a Sequence Listing which has been submitted in ASCII format via EFS-Web and is hereby incorporated by reference in its entirety. Said ASCII copy, created on Apr. 10, 2012, is named UTMB1032_Sequence_Listing_ST25.txt and is 5,381 bytes in size.

BACKGROUND OF THE INVENTION

Without limiting the scope of the invention, its background is described in connection with single stranded DNA aptamers and their therapeutic and diagnostic applications.

U.S. Patent Application No. 20080261225 (Ahn and Yang, 2008) discloses a method and a kit for detecting a target protein in a sample with a signal amplification strategy are provided. The signal amplification strategy is established for the aptamer-based molecular recognition of a target protein with concomitant release of single-stranded DNA (G-DNA), which binds complimentarily to a single-stranded RNA comprising a fluorophore and a quencher ("F-RNA-Q"). The fluorescence-quenched RNA is then degraded by RNase H to result in a fluorescence signal, and the undamaged G-DNA is recycled to yield fluorescence amplification.

U.S. Pat. No. 6,867,289 issued to Gorenstein et al. (2005) relates the generation of aptamers and to the use of aptamers as diagnostic and therapeutic agents. More particularly, the Gorenstein invention relates to methods using combinatorial chemistry to prepare aptamers having controlled thiophosphate replacement in the phosphate backbone for improved binding efficiencies to a target and to RNA and/or DNA products having novel nucleotide sequences and enhanced target binding efficacies.

U.S. Pat. No. 7,309,786 issued to Zhang et al. (2007) relates to a group of new oligonucleotides sequences with human tumor necrosis factor α (TNF-α) inhibiting activity, which includes DNA sequences and RNA sequences. These oligonucleotides or aptamer can specifically be bound to TNF-α and inhibit the cytoxicity of TNF-α to L929 cells. The aptamers taught by Zhang can be used to detect TNF-α and provide a therapeutic method for diseases related to the increasing level of TNF-α. Compared with other TNF antagonists such as monoclonal antibody and soluble receptor. The aptamers by Zhang are also said to have high specificity, high affinity, quick penetration to target tissue, rapid plasma clearance, and lower immunogenicity. Furthermore, it can be used repeatedly and keeps high concentration in target tissue and the like. It has the advantages of affinity and specificity similar to monoclonal antibodies and also has permeability and pharmacokinetics characteristics similar to small molecular polypeptide. Zhang also refers to derivative of the oligonucleotides sequence, including modified sequence. Finally, the aptamers taught by Zhang may further be manufactured as medicine for therapy and diagnosis of TNF-α related diseases.

SUMMARY OF THE INVENTION

The present invention describes the first identification of single stranded DNA aptamers that recognize NFkB RelA. These aptamers bind to several distinct regions of RelA and may be useful to antagonize the DNA binding of RelA as an inhibitor of cellular inflammation, visualize the location or amount of RelA in tissues from pathological conditions or to quantitatively measure the activated state of RelA by affinity binding.

In one embodiment the instant invention relates to one or more single stranded oligonucleotide sequences for binding to a target, wherein the oligonucleotide sequence is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21. In one aspect the one or more targets are selected from the group consisting of a protein, an antibody, a transcription factor, a ligand, a natural compound, a synthetic peptide, a candidate compound for a new drug, or any combinations thereof. In a specific aspect the target is an activated Nuclear Factor-κB (NF-κB)/RelA complex. In another aspect the oligonucleotide sequence is at least 90% homologous to a sequence comprising GCGGGACAGGAGAAACACGGCATGTCAGCG (SEQ ID NO: 21). In yet another aspect the oligonucleotide sequence is 100%, 97%, 94%, or 91% homologous to a sequence comprising GCGGGACAGGAGAAACACGGCATGTCAGCG (SEQ ID NO: 21). In one aspect the oligonucleotide sequence comprises SEQ ID NO: 9. In another aspect the oligonucleotide sequence is used in in vitro and in vivo quantification of RelA, isolation of RelA, purification of RelA, and any combinations thereof.

Another embodiment disclosed herein relates to one or more single stranded oligonucleotide sequences that specifically bind to an activated Nuclear Factor-κB (NF-κB)/RelA complex, wherein the oligonucleotide sequence is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21. In one aspect the oligonucleotide sequence is used in in vitro and in vivo quantification of RelA, isolation of RelA, purification of RelA, and any combinations thereof. In a related aspect the oligonucleotide sequence is at least 90% homologous to a sequence comprising GCGGGACAGGAGAAACACGGCATGTCAGCG (SEQ ID NO: 21). In another aspect the oligonucleotide sequence is 100%, 97%, 94%, or 91% homologous to a sequence comprising GCGGGACAGGAGAAACACGGCATGTCAGCG (SEQ ID NO: 21).

The present invention also provides a single stranded oligonucleotide sequence for specifically binding to activated Nuclear Factor-κB (NF-κB)/RelA complex comprising SEQ ID NO: 9. The single stranded oligonucleotide sequence of the present invention is used for a quantification of a level of RelA in a cell, for isolation, purification or both of RelA, and for improving sensitivity, accuracy, limit of quantitation, signal/noise ratio, or any combinations thereof of an analytical method for RelA. In one aspect the analytical method is Liquid Chromatography (LC)-Selected Reaction Monitoring (SRM)-Mass Spectrometry (MS).

In yet another embodiment the instant invention provides a method for quantification of activated RelA in a cellular extract comprising the steps of: (i) providing the cellular extract comprising an unknown amount of the activated RelA, (ii) contacting the cellular extract with one or more beads or a probe comprising one or more immobilized oligonucleotide sequences capable of binding the activated RelA, wherein the oligonucleotide sequence is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21 (iii) binding the activated RelA with the one or more oligonucleotide sequences on the bead or the probe, (iv) releasing the activated RelA bound to the oligonucleotide sequences from the one or more beads or the probe, and (v) assaying the released RelA by one or more analytical techniques.

In yet another embodiment the present invention discloses a method for improving sensitivity, accuracy, limit of quantitation, signal/noise ratio, or any combinations thereof of a Selected Reaction Monitoring (SRM)-Mass Spectrometry (MS) method for RelA comprising the steps of: (i) providing a sample comprising activated RelA for SRM-MS analysis, (ii) contacting the sample with one or more beads comprising immobilized oligonucleotide sequences capable of binding the activated RelA, wherein the oligonucleotide sequence is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21, (iii) incubating the sample with the one or more beads to facilitate the binding the activated RelA with the one or more oligonucleotide sequences on the bead, (iv) releasing the activated RelA bound to the oligonucleotide sequences from the one or more beads, and (v) assaying the released activated RelA by SRM-MS analysis.

The present invention also provides a method of enriching, isolating or both activated RelA from a cellular extract comprising the steps of: providing the cellular extract comprising the activated RelA, adding biotin conjugated single stranded oligonucleotide sequences capable of specifically binding the activated RelA, wherein the oligonucleotide sequence is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21, adding one or more streptavidin coated magnetic beads to capture the activated RelA bound to the oligonucleotide sequence, and digesting the beads to release the bound RelA.

Another embodiment disclosed herein details a method of enhancing isolation, affinity purification or both RelA during manufacture or downstream processing comprising the steps of: adding one or more beads or probes comprising an immobilized oligonucleotide sequences capable of binding the activated RelA, wherein the oligonucleotide sequence comprises SEQ ID NO: 9 to a cellular extract, a growth medium, an elution buffer, or any combinations thereof comprising activated RelA, binding the activated RelA from the cellular extract, a growth medium, an elution buffer or any combinations thereof to the oligonucleotide sequence on the bead or the buffer, and releasing the bound activated RelA from the bead or the probe, thereby enhancing isolation, affinity purification or both.

In another embodiment the present invention describes a method of modulating an innate immune response in a subject comprising the steps of: identifying the subject in need of modulation of the innate immune response; and administering to the individual a composition comprising one or more single stranded oligonucleotide sequences comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21, wherein the oligonucleotide sequences specifically bind to an activated Nuclear Factor-κB (NF-78 B)/RelA complex thereby leading to modulation of the innate immune response.

The present invention also discloses a method of inhibiting Nuclear Factor-κB (NF-κB) mediated gene expression in a subject or a cell comprising the step of transfecting into the cell or administering to the subject a composition comprising one or more single stranded oligonucleotide sequences comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21, wherein the oligonucleotide sequences specifically bind to an activated Nuclear Factor-κB (NF-κB)/RelA thereby inhibiting (NF-κB) mediated gene expression in the subject or the cell.

A testing kit for quantification of a level of activated RelA in a sample is disclosed in one embodiment of the present invention. The kit as described herein comprises: a first vial comprising one or more single stranded oligonucleotide sequences comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21, wherein the oligonucleotide sequences specifically bind to RelA, a second optional vial comprising reagents to detect the binding of the oligonucleotide sequences and RelA, and an instruction booklet comprising step-by-step directions for the usage of the kit.

A composition for imaging anatomical sites, determining extent of an inflammatory disease or disease state, determining effectiveness of a drug or a clinical trial, assessing individual response to the therapy, or any combinations thereof is disclosed in one embodiment of the present invention. The composition comprises: one or more single stranded oligonucleotide sequences comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21 conjugated with one or more contrast agents, microbubbles, liposomes, paramagnetic liposomes, or any combinations thereof, wherein the oligonucleotide sequences specifically bind to an activated Nuclear Factor-κB (NF-κB)/RelA complex.

Another embodiment of the present invention relates to a method for imaging anatomical sites, determining extent of an inflammatory disease or disease state, determining effectiveness of a drug or a clinical trial, assessing individual response to the therapy, or any combinations thereof in a subject comprising the steps if: identifying the subject in need of imaging the anatomical state, determination of the extent of the inflammatory disease or disease state, assessment of response to the therapy, or any combinations thereof, and intravenously administering a composition comprising one or more single stranded oligonucleotide sequences comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21 conjugated with one or more contrast agents, microbubbles, liposomes, paramagnetic liposomes, or any combinations thereof, wherein the oligonucleotide sequences specifically bind to an activated Nuclear Factor-κB (NF-κB)/RelA complex In yet another embodiment the present invention provides a composition for mediating tissue inflammation, treating cancer or both in a subject comprising: one or more single stranded oligonucleotide sequences comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21, wherein the oligonucleotide sequence is enclosed in a liposome, conjugated with one or more anti-proliferative agents, effector agents or any combinations thereof, wherein the oligonucleotide sequences specifically bind to an activated Nuclear Factor-κB (NF-κB)/RelA complex to inhibit the actions of NFκB/RelA in mediating tissue inflammation or cancer.

The present invention also relates to a method for mediating tissue inflammation, treating cancer or both in a subject comprising the steps of: identifying the subject in need of mediation of tissue inflammation, treatment of cancer or both and administering a therapeutically effective amount of a composition comprising: one or more single stranded oligonucleotide sequences comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or SEQ ID NO: 21 in an amount sufficient to mediate tissue inflammation, treat cancer or both, wherein the oligonucleotide sequence is enclosed in a liposome, conjugated with one or more anti-proliferative agents, effector agents or any combinations thereof, wherein the oligonucleotide sequences specifically bind to an activated Nuclear Factor-κB (NF-κB)/RelA complex to inhibit the actions of NFkB/RelA in mediating tissue inflammation or cancer.

BRIEF DESCRIPTION OF THE DRAWINGS

For a more complete understanding of the features and advantages of the present invention, reference is now made to the detailed description of the invention along with the accompanying figures and in which:

FIG. 9 shows the calibration curve for RelA SID-SRM assay. The linear regression analysis (1/x weighted) for RelA illustrates the linear dynamic range of the assay when analyte concentrations that respond non-linearly are excluded (o). The error bars indicate S.D. of the measurements;

FIGS. 10A-10D show comparisons between SRM assays of endogenous RelA in crude or aptamer-enriched fractions. RelA was measured in crude cellular fractions prepared from TNFα-stimulated A549 cells (10A and 10B) or cellular fractions subjected to aptamer-enrichment (10C and 10D): (10A) Extracted ion chromatogram of natural RelA peptide, (10B) extracted ion chromatogram of RelA SIS peptide, (10C) extracted ion chromatogram of RelA natural peptide, (10D) extracted ion chromatogram of RelA SIS peptide;

DETAILED DESCRIPTION OF THE INVENTION

Figures 1A, 1B:
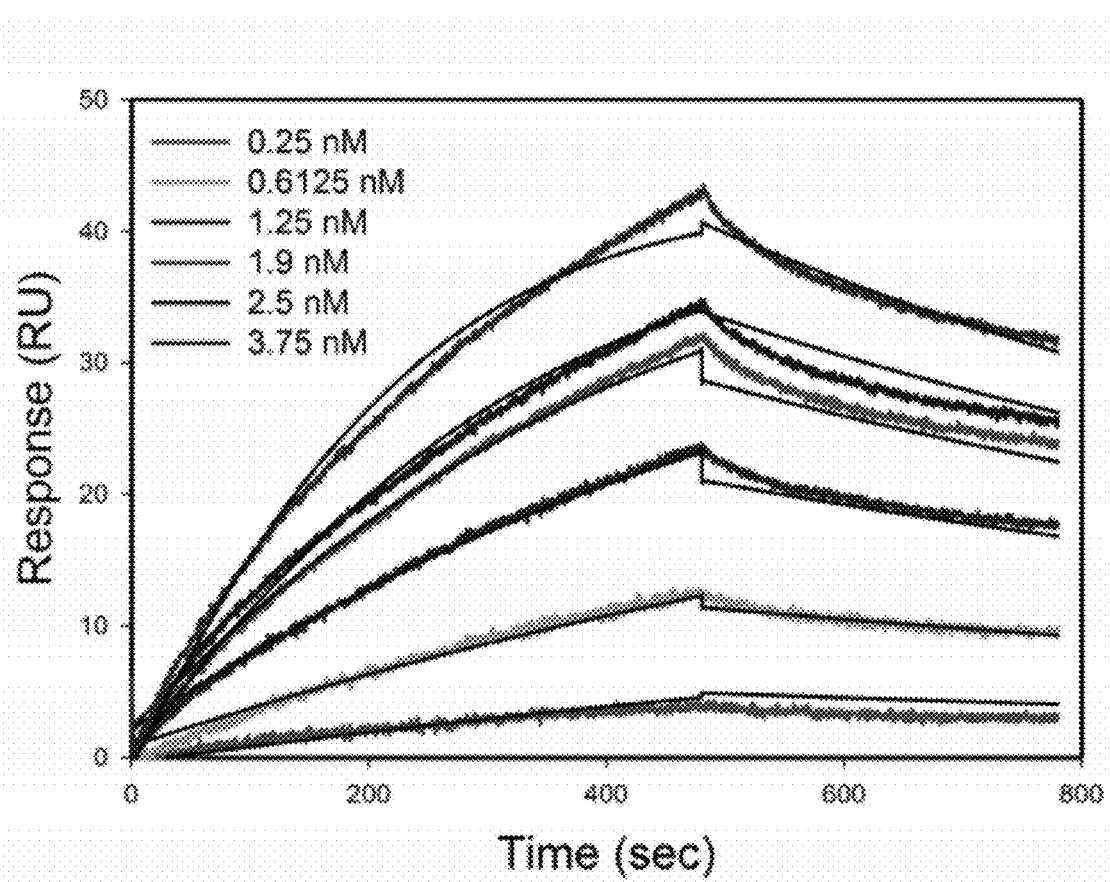
FIGS. 1A and 1B show the isolation of ssDNA aptamer binding to RelA (1-313): (1A) Sequences of P028F4 and nonspecific P028A1. Small case, flanking sequences and (1B) Sensorgram tracings for GST-RelA binding to P028F4. Increasing concentrations of GST-RelA (indicated in the inset) were used to bind to P028F4-coupled chip. Association and dissociation rates were measured for 8 and 5 minutes, respectively.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention describes the isolation of a ssDNA aptamer (termed P028F4) that binds to the activated (IκBα-dissociated) form of RelA and its application in an enrichment-mass spectrometric quantification assay for activated RelA.

The ssDNA P028F4 competes with cognate duplex high affinity NF-κB binding sites for RelA binding in vitro and also binds activated RelA in eukaryotic nuclei. P028F4 transfection into A549 cells reduces TNFα-stimulated endogenous NF-κB dependent gene expression. Incorporation of P028F4 as an affinity isolation step after initial enrichment with FLAG mAb enriches for Ser 536 phosphorylated- and p300 coactivator complexed RelA, simultaneously depleting IκBα·RelA complexes.

The present invention further described the development of a stable isotope dilution (SID)-SRM-MS assay for RelA that produced a linear response over 1,000 fold dilution range of input protein and had a 200 amol lower limit of quantification (S/N 85, 10.2% CV). This multiplex SID-SRM RelA assay was used to quantify activated endogenous RelA in cytokine-stimulated eukaryotic cells isolated by single-step P028F4 enrichment. The aptamer-SID-SRM-MS assay quantified the fraction of activated RelA in subcellular extract, detecting the presence of an inert cytoplasmic RelA reservoir unresponsive to TNFα stimulation. Thus, the aptamer-SID-SRM-MS of the present invention is a versatile tool for quantification of activated NF-κB/RelA and its associated complexes in response to pathway activation.

The innate immune response (IIR) is a stereotypic cellular response to alarmins, defensins and pathogen-associated molecular patterns that initiates inflammation, secretion of anti-microbial proteins and produces adaptive immunity (1,2). A major intracellular effector pathway of the IIR involves nuclear factor-κB (NF-κB), a ubiquitous family of highly inducible cytoplasmic transcription factors that control the expression of genetic networks that both initiate mucosal inflammation and later terminate the IIR (3,4). Nuclear Factor-κB (NF-κB) is a family of TNFα-inducible transcription factors regulated by stimulus-induced protein interactions. In the cytoplasm, the potent RelA transactivator is inactivated by binding inhibitory IκBs, whereas in its activated state, the serine-phosphorylated protein binds the p300 histone acetyltransferase.

In unstimulated cells, the NF-κB/RelA transcriptional activator is inhibited by binding to the IκB inhibitory proteins, resulting in cytoplasmic retention and inactivation of its DNA-binding activity (5). NF-κB/RelA activation is mediated by ligand-bound cell surface cytokine- or pattern recognition receptors. Here, receptor-associated adapter proteins are modified by Lys 63-linked polyubiquitylation, a post-translational modification that is recognized by the ubiquitin binding domain of the IKK regulatory subunit (6), recruiting IKK into the submembranous complex (7,8). This molecular interaction produces serine (Ser) phosphorylation in the IKK activation loop (9). Subsequently IKK dissociates back into the cytoplasm where it phosphorylates the IκBα $NH_2$ terminal regulatory domain on two adjacent Ser residues (10). Phospho-IκBα is then selectively degraded within the complex (11,12).

Liberated from its IκBα inhibitor, RelA rapidly enters the nucleus. A parallel pathway, required for NF-κB transactivation, produces RelA phosphorylation at Ser residue 536- or 276 (13-16). This event is required for binding the p300 coactivator, stimulating -Lys 310 acetylation (17), a posttranslational switch that enhances NF-κB binding, forming a transcriptionally active enhanceosome, modifying histones of target gene promoters and inducing proteolytic clearance of promoter-bound RelA through the ubiquitin proteasome pathway (13). In this way, subcellular localization, transcriptional activity and protein turnover of NF-κB is controlled by coupled inducible posttranslational modifications that affect protein-protein interactions.

A significant technical advance in systematic discovery of protein interaction networks has been the development and refinement of the tandem affinity purification (TAP) technique (18). In this technique, an affinity epitope-tagged "bait" protein is expressed and bait-associated complexes are isolated under native conditions by sequential affinity isolation. Using TAP, the interactome of 32 major regulators of the NF-κB pathway was determined, identifying over 680 nonredundant interacting proteins, representing 171 of 241 previously reported protein interactions (19). Bioinformatics filtering to eliminate nonspecific and high abundance contaminants reduced the interacting proteins to 131 "high confidence" interactors (19).

Methods that selectively isolate activated NF-κB/RelA complexes increase the understanding of the biochemistry of its transcriptional activation. To this end, selective enrichment of ssDNA oligonucleotides ("aptamers") that selectively bind the activated state of target proteins may have an important role in understanding the abundance and interaction network of activated complexes. The present inventors report herein an aptamer that stably binds and selectively isolates the activated state of NF-κB RelA. ssDNA aptamer P028F4 binds and associates with activated NF-κB/RelA in eukaryotic nuclei, and inhibits its association with endogenous promoters within the chromatin environment. Incorporation of aptamer P028F4 as an affinity isolation step after enrichment with FLAG binding enriches for RelA in its Ser 536 phosphorylated and p300-complexed state, while depleting inactive IκBα·RelA complexes. The inventors demonstrate that an aptamer enrichment technique coupled to absolute protein quantification using SID-SRM-MS can be used to quantify the fraction of activated RelA in cytokine-stimulated eukaryotic cells. This method is a versatile tool for quantification of activated NF-κB/RelA and analysis of its associated complexes that will further extend systems approaches to understand the NF-κB interactome.

Materials: Sequence grade modified trypsin was purchased from Promega (Madison, Wis.). Anti-FLAG M2 Affinity Gel and 3×FLAG peptide were from Sigma-Aldrich (St. Louis, Mo.), Nanolink Streptavidin Magnetic Beads were from Solulink (San Diego, Calif.) and recombinant TNFα was from PeproTek (Rocky Hill, N.J.). Antibodies used were: anti-RelA and anti-α-tubulin rabbit polyclonal Ab were from Santa Cruz Biotechnology (Santa Cruz, Calif.); anti-lamin B Ab was from Calbiochem (San Diego, Calif.); and anti-histone H3 was from Cell Signaling (Danvers, Mass.).

Recombinant protein expression: The cDNA encoding human RelA (aa 1-313) was PCR amplified and cloned into pGEX-KG expression plasmid to encode 67 kDa GST-RelA (1-313) fusion protein. The cDNA for full length hIκBα was amplified, cloned into pGEX-KG and transformed into E. coli XL1-Blue. Protein expression was induced using 1 mM Isopropyl β-D-1-thiogalactopyranoside for 4 h at 37° C. GST-tagged proteins were purified to near homogeneity using glutathione agarose affinity chromatography and dialyzed against HBS (20 mM HEPES pH 7.4, 150 mM NaCl). Protein was stored in aliquots at −20° C. in 50% glycerol.

Aptamer selection: DNA aptamers were selected following genetic enrichment protocols (20,21). A DNA library consisting of a 30 base random sequence flanked by 25 base common primer binding sites was commercially synthesized (Integrated DNA Technologies). Screening was performed by incubating GST-RelA protein with the aptamer pool in aptamer binding buffer ABB (20 mM Tris-HCl pH 7.4, 150 mM NaCl and 1 mM $MgCl_2$) for 30-60 min at RT, followed by separation of the free DNA from the bound DNA by filtering through a 25 mm diameter nitrocellulose filter (Millipore). DNA was eluted from the filter with a 72° C. incubation in elution buffer (0.25% SDS, 20 mM Tris-HCl, pH 7.5, 1 mM EDTA) for 30 minutes and ethanol precipitated. The eluted DNA was quantified using quantitative real-time PCR (Q-PCR). The eluted DNA was PCR amplified using a biotinylated (Bt) reverse primer and an unmodified forward primer. The amplified material was bound to Streptavidin (SA)-paramagnetic beads (Solulink, Inc) in bead binding buffer (20 mM Tris-HCl, pH 7.5, 1 mM EDTA, 200 mM NaCl and 0.01% Triton-X), and washed with binding buffer without detergent. The non-Bt single strand was eluted with 0.15N NaOH at room temperature. The DNA was ethanol precipitated, dissolved in TE and quantified using a Nanodrop 1000 instrument (ThermoFisher, West Palm Beach, Fla.). At several points during the selection rounds the aptamer pool was incubated with a nitrocellulose filter to remove filter binding aptamers. Sequences of the amplifying primers were Forward, 5'-GGTAACCTTGAGTC ACGAATTCAA-3' (SEQ ID NO: 1); Reverse, 5'-CAGAAGCTGTAAG TTGGGTAC-CTT-3' (SEQ ID NO: 2).

Q-PCR assays and filter binding assays were used to determine when the aptamer pool was enriched with RelA binding species. The enriched pool was PCR amplified with unmodified primers and cloned with a TOPO-Blunt cloning kit (Invitrogen, Carlsbad, Calif.). Individual clones were picked and characterized for RelA binding. Positive clones were sequenced by the UTMB Molecular Genomics core and analyzed using Sequencher software (Genecodes, Ann Arbor, Mich.).

Binding Studies: (i) Nitrocellulose filter binding assay: Filter binding assays were performed as described (22). Initially, 70 mer oligonucleotides were commercially synthesized (IDT) to include the proximal 20 bases of each flanking primer sequence and the 30 base variable region. DNAs were 5' end-labeled with $^{32}$P-ATP using T4-PNK (New England Biolabs) and purified by glass bead binding using a MERMAID kit (MP Biomedicals LLC). Protein and labeled aptamer were incubated in ABB and filtered through 25 mm nitrocellulose filters. The bound material was counted in a Beckman Liquid Scintillation counter. For competition studies, binding reactions (100 μL) in ABB were incubated at RT for 20 min with 100 fold excess (10 picomoles) of unlabeled competitor DNAs, followed by the addition of 0.1 picomole of $^{32}$P-labeled KB55 probe. After 30 min of incubation, reactions were filtered and counted. The KB55 sequence is ATACGGGAATTCCCG (SEQ ID NO: 3) and self anneals to form a duplex. Upper and lower strands of IL8KB are ACT-AGGAATTTCCAGTG (SEQ ID NO: 4) and CACTG-GAAATTCCTAGT (SEQ ID NO: 5), respectively.

(ii) Surface Plasmon Resonance (SPR): 5'-Bt aptamer was attached to a CM5-streptavidin (SA) chip (GE Healthcare) to a level of 20-30 RUs in a Biacore T1000. Running buffer was HBS-T (20 mM HEPES ph 7.4, 150 mM NaCl and 0.01% Triton X) with 100 µg/L sheared salmon sperm DNA. GST-RelA was dialyzed against HBS-T and injected onto the chip at the indicated concentrations. Binding kinetics was determined using the Biacore software.

Cell culture: Human A549 pulmonary epithelial cells were grown in F12K medium as described (23-25). Full length human RelA was expressed as a FLAG-EGFP fusion protein in A549 cells using the pCX4-Pur expression vector (26).

Preparation of cellular extracts: (i) Cytoplasmic (CE) and nuclear extracts (NE): A549 cells were scraped and subjected to hypotonic buffer/detergent lysis (27). The supernatant (CE) was saved and the nuclear extract (NE) was purified by centrifugation through a sucrose cushion followed by extraction in Buffer C (50 mM HEPES, pH 7.9, 10% glycerol, 400 mM KCl, 1 mM EDTA, 1 mM EGTA, 1 mM DTT, 0.1 mM PMSF) with protease inhibitor cocktail (Sigma Aldrich, St. Louis, Mo.) (27, 28). Protein content was estimated by Coomassie Brilliant Blue staining using BSA as a standard (Bio-Rad, Hercules, Calif.).

(ii) Whole cell extracts (WCE): A549 cells were washed with PBS and lysed with WCE buffer (10 mM Tris-HCl, pH 7.4, 100 mM NaCl, 1 mM EDTA, 0.5% Triton X-100) supplemented with protease inhibitor cocktail and phosphatase inhibitor mix (PIERCE). Lysates were sonicated briefly and centrifuged at 10,000 g for 10 min at 4° C.

Confocal microscopy: EGFP-A549 cells were stimulated in the absence or presence of TNFα (30 ng/ml, 1 h). The cells were then trypsinized and nuclei isolated and counted. $2 \times 10^4$ nuclei were centrifuged (cytospin) into slides and fixed with 4% paraformaldehyde. After fixation, the slides were washed twice with PEM (0.1 M PIPES, pH 6.9, 1 mM EGTA, and 1 mM $MgCl_2$) buffer (29), and stained with the indicated TEX 615 (IDT)-conjugated aptamer (5 nM) overnight at 4° C. The following day, the nuclei were counterstained with DRAQ5 (2 mM), and washed in PEM buffer. The slides were air-dried, mounted, and images taken by LSM 510 confocal imaging system.

Western blot: Proteins were fractionated by 10% SDS-PAGE, electro-transferred to a polyvinylidene difluoride membrane, blocked, and probed with the indicated primary Ab (13,23,30). Washed membranes were incubated with IRDye 700-conjugated anti-mouse Ab or IRDye 800-conjugated anti-rabbit Ab (Rockland Inc., Gilbertsville, Pa.) and imaged by an Odyssey infrared scanner (LiCor, Lincoln, Nebr.).

Electrophoretic Mobility Shift Assays (EMSAs): NE (15 µg) were incubated with 40,000 cpm of $^{32}P$-labeled duplex Naf-1 WT probe oligonucleotide probe and 2 µg of poly (dA-dT) in binding buffer (8% glycerol, 100 mM NaCl, 5 mM $MgCl_2$, 5 mM dithiothreitol, and 0.1 µg/ml phenylmethylsulfonyl fluoride) in a final volume of 20 µL, for 20 min at RT. The complexes were fractionated on a 6% native PAG. The duplex DNA corresponding to the NF-κB binding site in the Naf-1 gene was used as a probe (31). Competition was performed by the addition of 100-fold molar excess nonradioactive competitor.

Quantitative Reverse Transcriptase PCR (Q-RT-PCR): One µg of total RNA was reverse-transcribed using Super Script III in a 20 µL reaction mixture. One µL of cDNA product was amplified in a 20 µL reaction mixture containing 10 µL of SYBR Green Supermix (Bio-Rad) and 0.4 M each of forward and reverse gene-specific primers (24,32). The plates were denatured for 90 sec at 95° C. and then subjected to 40 cycles of 15 sec at 94° C., 60 sec at 60° C., and 1 min at 72° C. in an iCycler (BioRAD). Quantification of changes in gene expression was using the ΔΔCt method using unstimulated cells as the calibrator (32).

Two-Step Chromatin Immunoprecipitation (ChIP) assay: Two-step ChIP was performed in intact cells as described (33,34). De-cross-linked DNA was determined by quantitative real-time genomic PCR (Q-gPCR) using promoter-specific primers. Standard curves were generated using a dilution series of genomic DNA (from 40 ng-25 µg) for each primer pair (34). The fold change of DNA in each immunoprecipitate was determined by normalizing the absolute amount to input DNA reference and calculating the fold change relative to that amount in unstimulated cells.

Aptamer-Tandem Affinity Purification of RelA: (i) Affinity isolation of FLAG tagged RelA: Indicated concentrations of WCE from FLAG-EGFP-RelA-expressing A549 cells were incubated with anti-FLAG M2 Affinity Gel 16 h at 4° C. The beads were washed with chilled WCE buffer four times by centrifugation (5K, 2 min, 4° C.). The FLAG-EGFP-RelA was eluted by addition of 150 µg of 3×FLAG peptide (35) and incubated with mixing for 1 h at 4° C. The mixture containing FLAG-EGFP-RelA protein complex and gel were filtered through empty spin column (BioRad) and the flow-through collected.

(ii) Affinity isolation of aptamer-bound RelA: Bt-Aptamer was added to final concentration of 20 nM in FLAG-EGFP-RelA for 2 h at 4° C. During this time, 20 µL slurry of SA-Magnetic Beads were pre-blocked by dilution with 300 µL WCE buffer and 200 µL acetylated casein (0.2 mg/ml) at RT for 2 h, followed by 3 washes in WCE buffer. Bt-aptamer bound FLAG-EGFP-RelA was added to the SA-Magnetic beads and incubated for 20 min at 4° C. Bt-aptamer bound protein complex was separated from free complex on a magnetic stand and beads washed 6 times with WCE buffer. 50 µL SDS sample loading buffer was added to the washed beads, boiled, and protein complex was separated from SA-beads using a magnetic stand.

Selective Reaction Monitoring (SRM) Assays: (i) Selection of High Responding Signature Peptides: Signature peptides that stoichiometrically represent the protein candidate were selected on the following criteria: uniqueness for the target protein; length of 8-25 residue; and absence of missed tryptic cleavages, chemically active amino acid residues (such as cysteine or methionine), and no basic amino acids on either cleavage site of the peptide sequence (36). In order to achieve the maximum sensitivity, these signature peptides should be the highest MS responding peptides for each protein. Pilot LC-MS-MS experiments were performed using tryptic digests of affinity-purified RelA or IκBα. The extracted ion chromatograms based on the monoisotopic peak for all charge states and modifications detected from sequence-identified peptides were compared and the peptides with highest MS response were selected. The selected high responding signature peptides for each target protein are listed in Table 1.

TABLE 1

SRM parameters of SRM assays of RelA and other proteins.
Masses listed are for the natural forms of the peptides.
Abbreviations: Coll., collision; Q, quadropole.

| Protein name | Gene name | UniProt accession no. | Peptide Sequence | Peptide molecular mass (Da) | Q1 | Q3 | Coll. Energy (V) | Fragment ion |
|---|---|---|---|---|---|---|---|---|
| Transcription factor p65 | RelA | Q04206 | TPPYADPSLQAPVR (SEQ ID NO: 6) | 1510.792 | 756.396 | 867.504 | 30 | y8 |
| | | | | | 756.396 | 982.531 | 24 | y9 |
| | | | | | 756.396 | 1053.568 | 26 | y10 |
| | | | | | 756.396 | 1313.684 | 26 | y12 |
| NF-kappa-B inhibitor alpha | IκBα | P25963 | LEPQEVPR (SEQ ID NO: 7) | 966.528 | 484.264 | 500.282 | 20 | y4 |
| | | | | | 484.264 | 628.341 | 20 | y5 |
| | | | | | 484.264 | 725.394 | 20 | y6 |
| | | | | | 484.264 | 854.436 | 20 | y7 |
| | | | | | 484.264 | 967.52 | 20 | y8 |
| Actin, cytoplasmic 1 | ACTB | P60709 | AVFPSIVGR (SEQ ID NO: 8) | 944.558 | 473.279 | 531.324 | 19 | y5 |
| | | | | | 473.279 | 628.377 | 19 | y6 |
| | | | | | 473.279 | 775.446 | 19 | y7 |
| | | | | | 473.279 | 874.514 | 19 | y8 |

(ii) Synthesis of Native and Stable Isotopically Labeled Peptide Standards (SIS): Native tryptic peptides were synthesized using N-(9-fluorenyl) methoxycarbonyl chemistry. SIS peptides were commercially synthesized incorporating isotopically labeled [$^{13}C_6^{15}N_4$] Arginine to a 98% isotopic enrichment (Sigma Aldrich). Both native and SIS peptides were HPLC purified to >98% purity. The molecular weights were measured with electrospray mass spectrometry (ESI-MS) and matrix-assisted laser desorption/ionization time-of-flight mass spectrometry (MALDI-TOF MS). The specific peptide concentration was determined by amino acid analysis. Individual SIS peptide stocks of 20 pmol/μL were made in 80% ACN.

Trypsin digestion of subcellular protein extracts: Protein extracts were denatured with 8 M guanidinium HCl and a 50 μg aliquot of each sample was reduced with 10 mM DTT for 30 min at RT. Protein cysteinyl residues were alkylated with 30 mM of iodoacetamide for 2 h at 37° C. The samples were diluted 10-fold with 100 mM ammonium bicarbonate, and digested with 2 μg of trypsin overnight at 37° C. The trypsin digestion was stopped by adding 10% TFA. The volume of each sample was adjusted with water to 400 μL. The tryptic digests were dried and resuspended in 5% formic acid-0.01% TFA prior to SID-SRM-MS analysis.

SIS peptide stocks were diluted to a concentration of 10 fmol/μL with 0.01% TFA. Before LC-SRM-MS analysis, 30 μL of each tryptic digest was mixed with 10 μL of each SIS peptide. These sample solutions were directly used for SID-SRM-MS analysis without further purification or fractionation.

Quantification of activated fraction of endogenous RelA: (i) Single step aptamer isolation of endogenous RelA: A549 cell CE and NE were prepared from control or TNFα stimulated cells (30 ng/ml, 45 min). Bt-aptamer was added to a final concentration of 20 nM, and incubated for 2 h at 4° C. A 20 μL slurry of acetylated casein-preblocked SA-Magnetic Beads was added and binding continued at 4° C., 20 min, followed by 3 washes in WCE buffer and 3 washes in PBS.

(ii) On-beads Tryptic digestion: The beads were resuspended in 30 μL of 50 mM ammonium hydrogen carbonate (pH 7.8) and 20 μL of 0.1 μg/μL of trypsin was added. The samples were mixed and trypsinized by gentle vortexing overnight at 37° C. After digestion, the supernatant was collected. The beads were washed with 50 μL of 50% ACN three times and the supernatant was pooled, and dried. The tryptic digests were then reconstituted in 30 μL of 5% formic acid-0.01% TFA. An aliquot of 10 μL of diluted SIS peptides were added to each tryptic digest. The final concentration of each SIS peptide was 2.5 fmol/μL. These sample solutions were directly used for LC-SRM-MS analysis without further purification or fractionation.

LC-SRM-MS Analysis: LC-SRM-MS analysis was performed with a TSQ Vantage triple quadrupole mass spectrometer equipped with nanospray source (ThermoFinnigan, San Jose, Calif.). The online desalting and chromatography were performed using an Eksigent NanoLC-2D HPLC system (AB SCIEX, Dublin, Calif.). An aliquot of 10 μL of each of tryptic digests were injected on a C18 peptide trap (Agilent, Santa Clara, Calif.), desalted with 0.1% formic acid at a flow rate of 2 μL/min for 45 min. Peptides were eluted from the trap and separated on a reverse-phase nano-HPLC column (PicoFrit™, 75 μm×10 cm; tip ID 15 μm) packed in house using Zorbax SB-C18 (5-μm diameter particles, Agilent, Santa Clara, Calif.). Separations were performed using a flow rate of 500 nL/min with a 20-min linear gradient from 2-40% mobile phase B (0.1% formic acid-90% acetonitrile) in mobile phase A (0.1% formic acid), followed by 0.1-min gradient from 40-90% mobile phase B and 5-min 90% mobile phase B. The TSQ Vantage was operated in high-resolution SRM mode (h-SRM) with Q1 and Q3 set to 0.2 and 0.7-Da Full Width Half Maximum (FWHM). All acquisition methods used the following parameters: 1800 V ion spray voltage, a 275° C. ion transferring tube temperature, a collision-activated dissociation pressure at 1.5 mTorr, and the S-lens voltage used the values in S-lens table generated during MS calibration. Each sample was analyzed by LC-SRM-MS twice.

SRM Data Analysis: All SRM data were processed using Xcalibur® 2.1. The default values for noise percentage and base-line subtraction window were used. All data were manually inspected to ensure peak detection and accurate integration. The chromatographic retention time and the relative product ion intensities of the analyte peptides were compared to those of the SIS peptides. The variation of the retention time between the analyte peptides and their SIS counterparts should be within 0.05 min, and no significantly difference in the relative product ion intensities of the analyte peptides and SIS peptides were observed. For the SRM-MS analysis of crude protein extracts, β-actin was used as loading control. All of the measured natural verse SIS standard peptide ratios were normalized against β-actin.

Isolation of RelA(1-313) binding single stranded aptamer: Purified recombinant GST-RelA(1-313), encoding the DNA binding and IκBα interactive domain, was used to screen for high affinity ssDNA aptamers by repeated rounds of in vitro binding and enrichment. After 12 rounds of selection, it was found that greater than 50% of the aptamer pool bound to the target RelA protein. Individual clones were obtained, the inserts were amplified by PCR, separated into single-strands, and tested for RelA binding. The inventors sequenced 9 clones that exhibited binding, and synthesized 70-mer oligonucleotides for each. Competition studies showed that 5 of the aptamers fall into the same group, competing with each other for binding; from this group, clone P028F4 for further studies. FIG. 1A shows the sequence of P028F4 including the primer flanking sequences. The variable region contains the sequence GGGAC, matching half of the double-strand NF-κB natural binding site GGGACTTTCC (SEQ ID NO: 18). The 4 other aptamers in this group also contained this sequence or the similar GGGCC. Competition and direct binding studies showed that the 30 base variable region by itself was sufficient for binding (data not shown). Secondary structure analysis using the UNAFold program (37) did not predict significant secondary structure, and there is no complement to the GGGAC sequence in the aptamer to allow it to form double-strand DNA. The inventors performed competition studies in nitrocellulose binding assays with natural double-strand binding sites (Table 2). Aptamer P028F4 was able to compete effectively for binding to the IL-8 NF-κB binding site. A non-specific control aptamer P028A1 did not compete as well for binding.

P028F4 binding affinity was determined by SPR measurement (FIG. 1B). The binding activity fit well to a 1:1 binding model with a $K_D$ of $6.4 \times 10^{-10}$, calculated from a $k_a$ of $1.8 \times 10^6$ l/M·s and kd of 0.0018 l/s. These estimates are similar to those obtained from nitrocellulose filter binding studies (data not shown).

TABLE 2

P028F4 competes with dsNF-κB for RelA (1-313) binding. Shown is percent P028F4 binding after competition with indicated unlabeled competitor.

| Competitor | Percent Binding |
| --- | --- |
| None | 100% |
| P028A1 | 77% |
| P028F4 | 0% |
| IL-8 | 32% |
| KB55 | 8% |

Figure 2A:
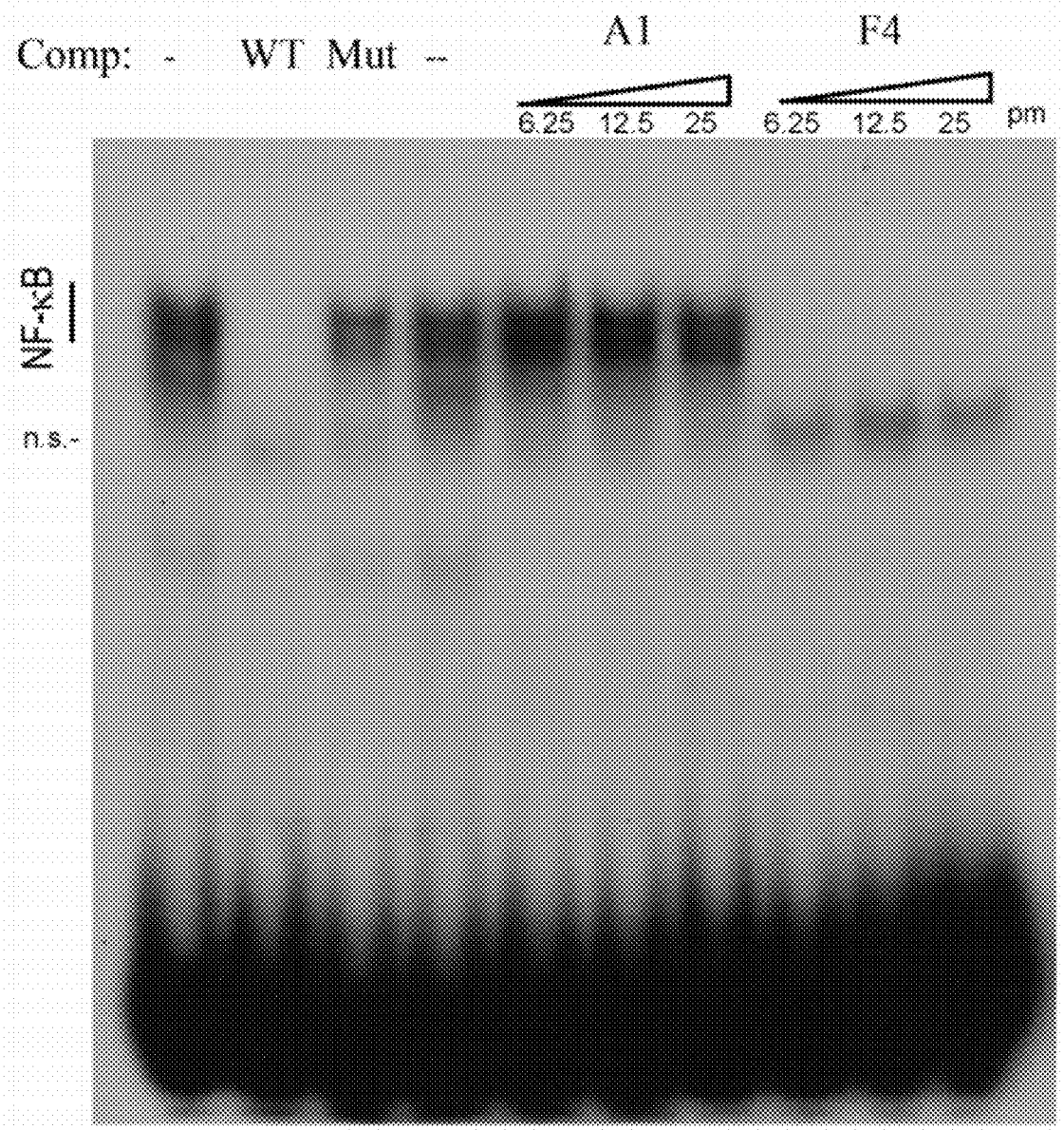
FIGS. 2A and 2B show the binding of P028F4 to activated RelA: (2A) EMSA using NE prepared from TNF stimulated A549 cells were incubated with 0.25 pmol of radiolabeled double-stranded (ds) NF-κB. Unlabeled ssDNA aptamers (P028A1 or P028F4) were incubated with NE in increasing concentrations prior to fractionation at 6.25, 12.5 and 25 pmol, representing 25-50- and 100-fold molar excess of probe as indicated. Shown is an autoradiogram of bound and free complexes. A1, P028A1; Comp, competitor; F4, P028F4; WT, wild-type NF-κB duplex; Mut, mutant NF-κB duplex; n.s., nonspecific; pm, pmol and (2B) EMSA using NE prepared from unstimulated (Con) or TNF-stimulated A549 cells using radiolabeled P028F4 as a probe. NE were incubated in the presence of 100-fold excess duplex wild-type NF-κB (WT) or duplex mutant NF-κB (Mut) competitors (Comp) prior to fractionation. Shown is an autoradiogram of the complexes.

Aptamer P028F4 binds RelA and competes with duplex dsNF-κB sequences for RelA binding: To confirm if aptamer P028F4 competes with duplex (ds) NF-κB binding sites, a competition-EMSA study was performed. NE prepared from control or TNFα-stimulated A549 cells was incubated with a radiolabeled dsNF-κB DNA binding site in the presence of increasing concentration of unlabeled P028A1 or P028F4. Native gel electrophoresis of the DNA-protein complexes showed a characteristic NF-κB complex (25,38). These complexes bound with NF-κB binding specificity, being competed with 100-fold molar excess of unlabeled dsNF-κB duplex, but not the corresponding site mutation (FIG. 2A). Although aptamer P028A1 did not disrupt the NF-κB complex, aptamer P028F4 competed effectively for dsNF-κB binding.

Figure 2B:
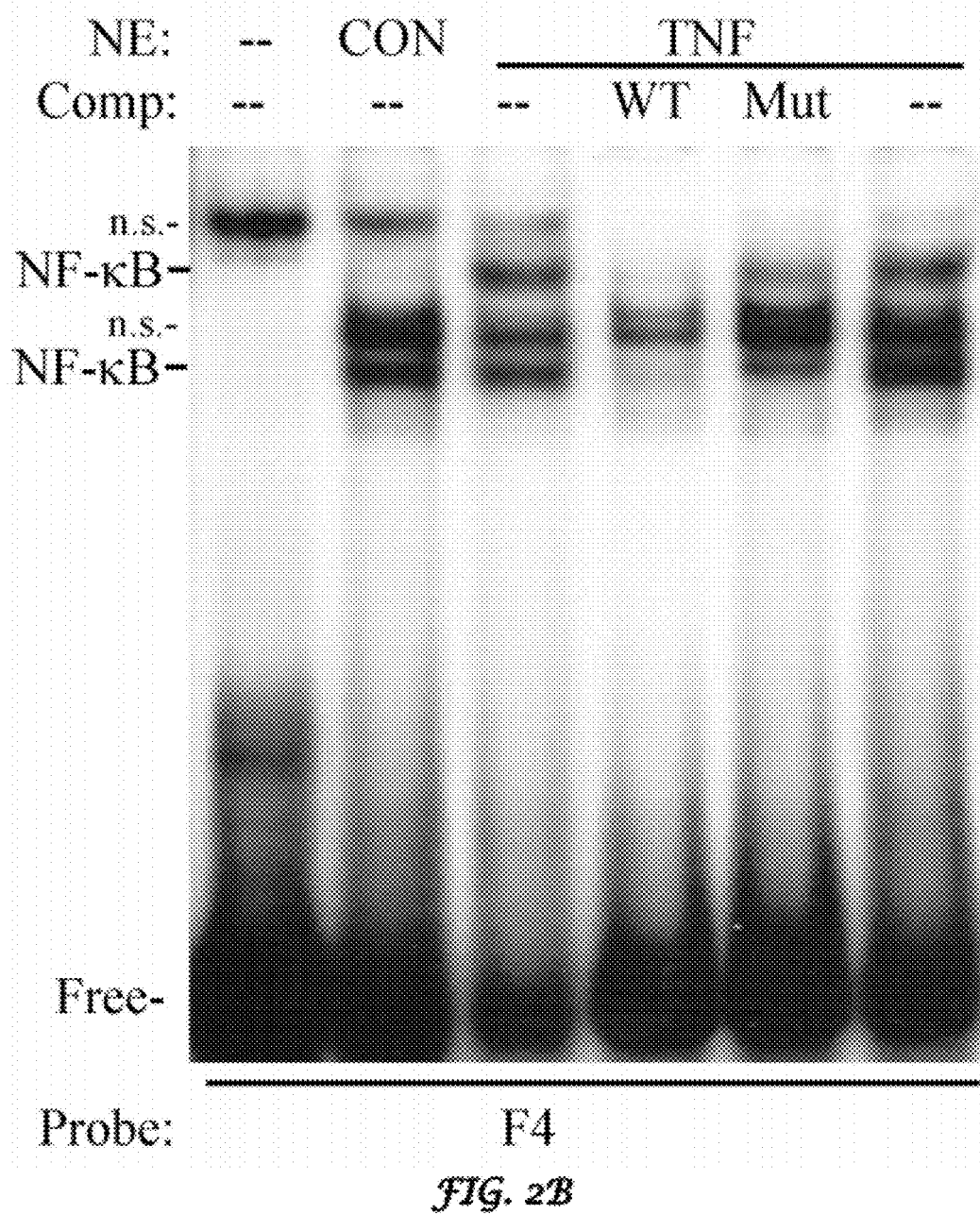

In a converse study, NE prepared from unstimulated or TNFα-stimulated A549 cells was directly bound to radiolabeled P028F4 as a probe in the presence of unlabeled specific or non-specific dsDNA competitor. In control NE, a complex of nonspecific proteins was detected on P028F4. Upon TNFα stimulation, two new nucleoprotein complexes were detected that represent specific NFkB complexes because they competed specifically with a 100-fold excess of unlabeled dsNF-κB wild type (WT), but not mutant (Mut) DNA sequences (FIG. 2B). Together, these data indicated that aptamer P028F4 competes for dsNF-κB binding to NF-κB/RelA.

Figure 3A:
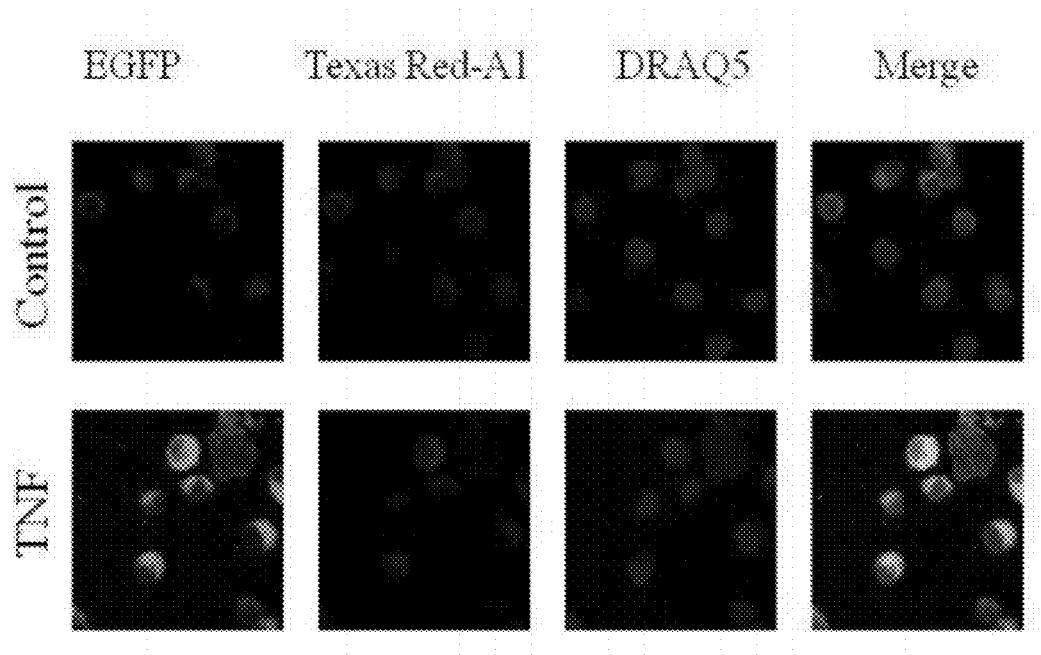
FIGS. 3A and 3B show that P028F4 colocalizes with activated nuclear RelA: (3A) Intact nuclei from control or TNF stimulated EGFP-RelA expressing A549 cells were stained with TEX 615 (Texas-Red)-conjugated P028A1 (5 nM). Nuclei were counterstained with DRAQ5 to define nuclear boundaries. Shown is a confocal microscopy image of the nuclei and (3B) TEX 615-conjugated P028F4 binding. Note the presence of nuclear EGFP-RelA in the presence of TNF, and strong TEX 615 staining in P028F4 stained nuclei. Merge, EGFP-TEX 615 merged image.
Figure 3B:
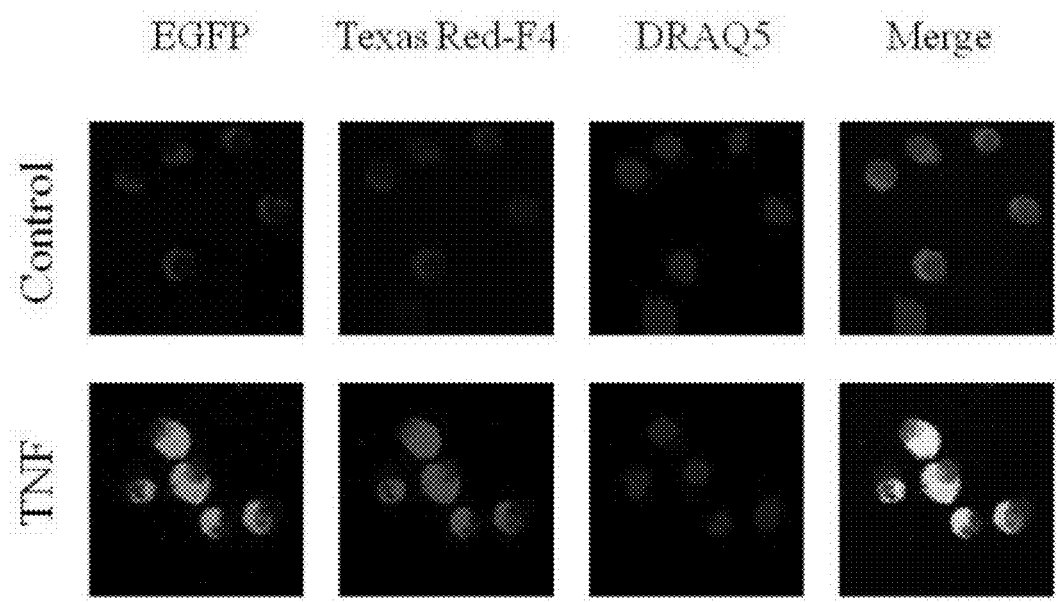

Aptamer P028F4 colocalizes with activated nuclear RelA: Other studies have shown that aptamers are bound nonspecifically to high abundance ssRNA binding proteins in cells (29); the present inventors also found that transfection of intact cells with chemically synthesized fluorescent TEX 615-conjugated P028A1 and P028F4 showed a high amount of nonspecific cytoplasmic staining, despite methods to reduce nonspecific interactions such as zwitterionic detergents [not shown, ref (29)]. To circumvent this problem, the inventors imaged intact nuclei from control or TNFα stimulated EGFP-RelA expressing A549 cells stained with TEX 615-conjugated P028A1 or P028F4 by confocal microscopy. In the absence of TNFα stimulation, little EGFP staining was detected (FIG. 3A). By contrast, upon TNFα stimulation, the nuclei were strongly stained with translocated EGFP-RelA. Nuclei treated with P028A1 were TEX 615-negative in the absence or presence of TNFα stimulation (FIG. 3A). By contrast, TNFα stimulated nuclei treated with P028F4 strongly stained TEX 615-positive, whereas control nuclei were negative (FIG. 3B). The merged images indicated colocalization. Together these data indicate that P028F4 colocalizes with activated EGFP-RelA in eukaryotic nuclei.

Figure 4A:
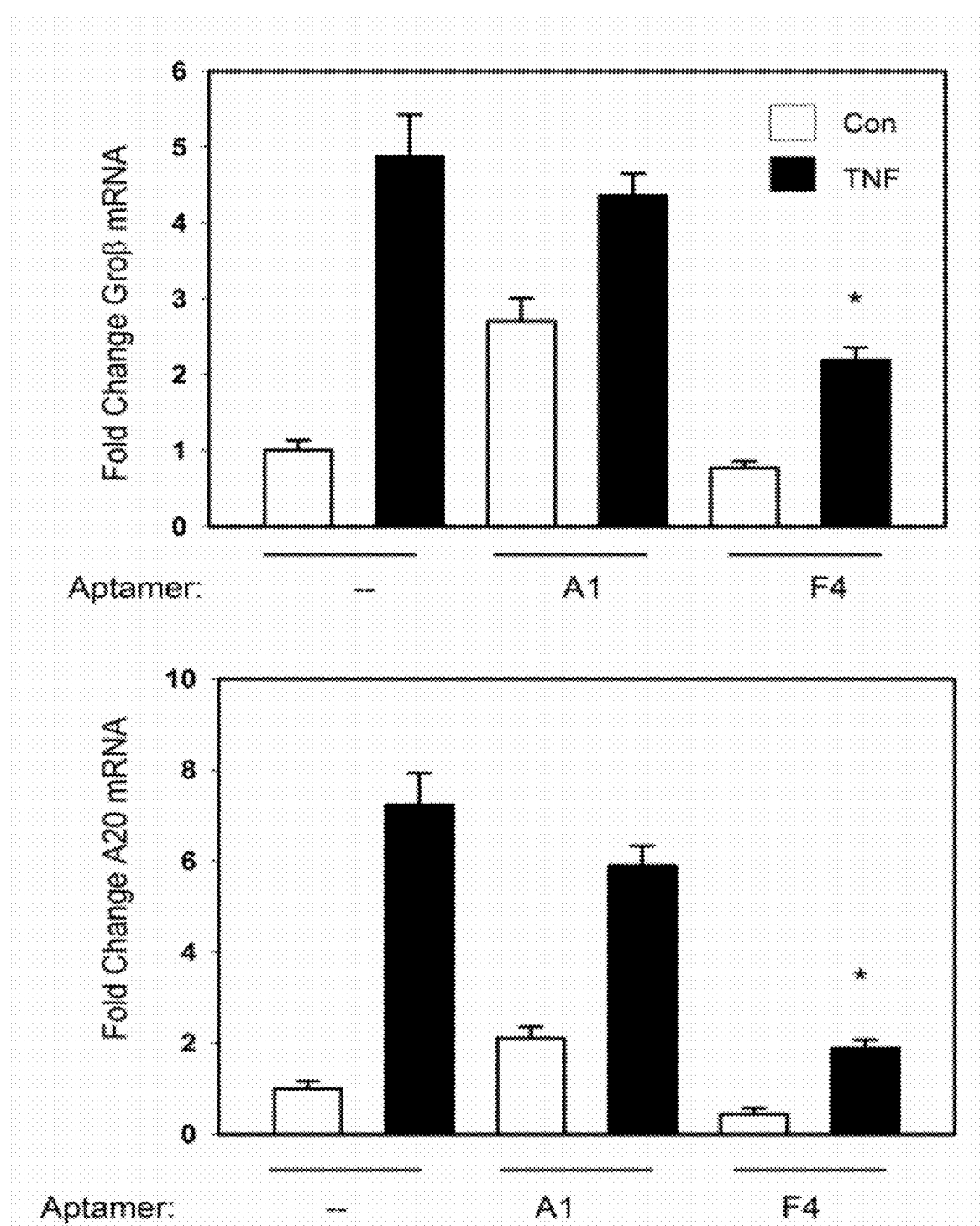
FIGS. 4A and 4B show that P028F4 inhibits TNF-induced endogenous NF-κB dependent gene expression: (4A) Q-RT-PCR. A549 cells transfected with nothing (−), 4 μM P028A1 or P028F4 aptamers were stimulated in the absence (Con) or presence of TNF. (1 h, 30 ng/ml). Total RNA was extracted and subjected to Q-RT-PCR for Gro-β (top panel) and TNFAIP3/A20 (bottom panel). Data are normalized to GAPDH and expressed as fold change relative to uninfected control. Each bar is mean±SD of triplicate determination. *p<0.05 and (4B) ChIP assay. A549 cells transfected with nothing (−), P028A1 (4 μM) or P028F4 (4 μM) were stimulated in the absence (Con) or presence of TNF (1 h, 30 ng/ml). Two-step ChIP was preformed using pre-immune IgG (IgG), or anti-RelA as the primary Abs. Immunoprecipitated DNA was subjected to quantitative PCR using primers for Groβ (top) or TNFAIP3/A20 promoters (bottom) as indicated. Data are shown as fold increase in signal relative to unstimulated A549 cells (X, ±SD of technical replicates). The study was repeated twice with similar results.

Aptamer P028F4 inhibits TNFα-induced endogenous NF-κB dependent gene expression: Earlier studies selectively inhibiting NF-κB/RelA translocation identified Groβ and TNFAIP3/A20 as part of a TNFα inducible gene network downstream of NF-κB (3,4,39). To determine whether P028F4 interfered with TNFα-induced NF-κB dependent gene expression, A549 cells were reverse transfected with nothing, P028A1 or P028F4 (4 μM respectively) and the cells were TNFα stimulated. Relative changes in Groβ and TNFAIP3/A20 transcripts were determined by Q-RT-PCR. In the absence of aptamer transfection, Groβ mRNA was induced 5-fold in response to TNFα (FIG. 4A, top). In cells transfected with P028A1, an inconsistent effect on unstimulated Groβ expression was observed, but this did not significantly reduce the Groβ expression induced by TNFα. By contrast, in P028F4-transfected cells, basal and TNFα-induced Groβ expression was significantly reduced to less than 2-fold induction. Similar qualitative results were observed for the expression of TNFAIP3/A20, where the nearly 7-fold induction observed in control transfected cells was reduced to less than 2-fold in P028F4-transfected cells (FIG. 4A, bottom). Importantly, each RNA sample was measured for expression of GAPDH as an internal control, where aptamer transfection had no effect on GAPDH mRNA levels. These observations indicated that transfected P028F4 had a consistent inhibitory effect on NF-κB dependent gene expression in vivo.

Figure 4B:
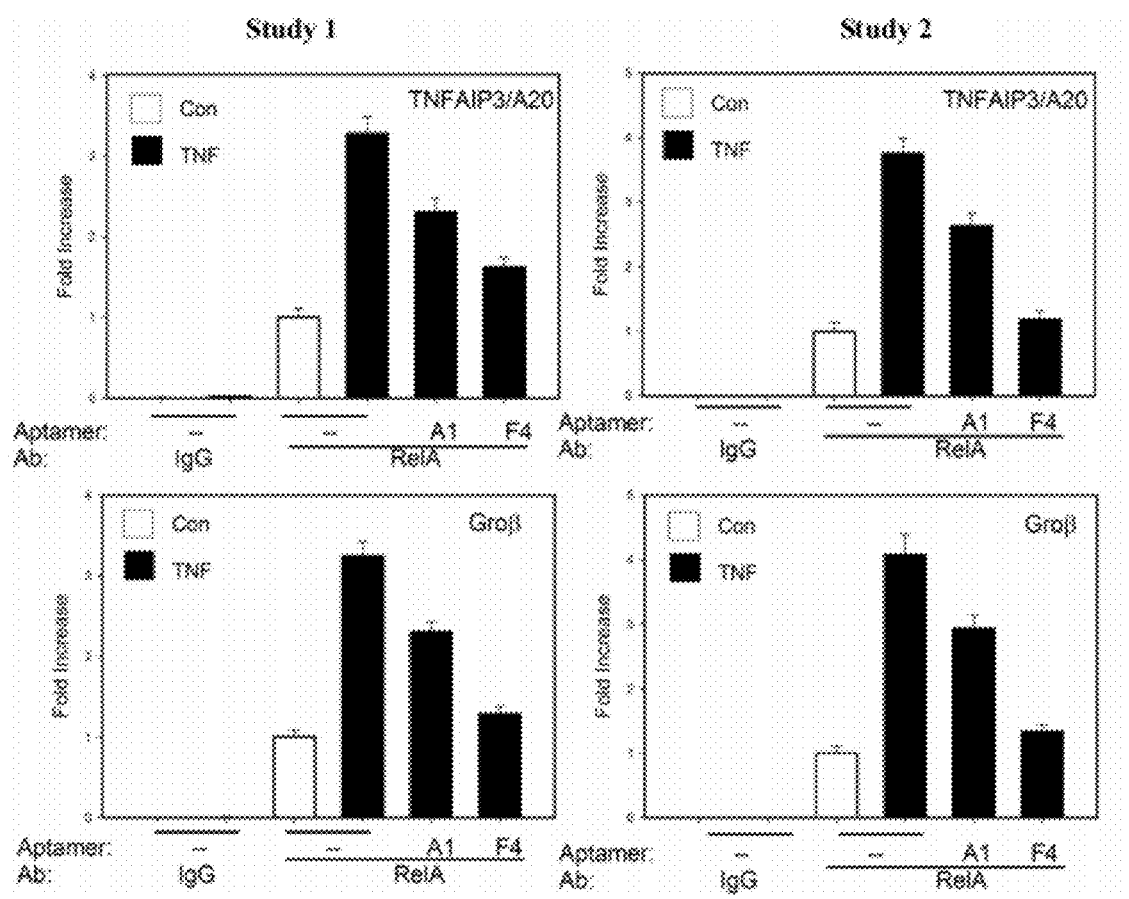

Aptamer P028F4 blocks RelA association with endogenous NF-κB dependent gene promoters in vivo: Previous studies using dynamic live-cell imaging have shown that RelA association with endogenous chromatin is hyperdynamic (40), in contrast to its stable association with DNA targets in vitro. This observation makes the ability of P028F4 to compete for RelA binding seen earlier in EMSA (FIG. 2) of uncertain relevance to the interaction of RelA with endogenous chromatin. To address this issue, aptamer-transfected A549 cells stimulated in the absence or presence of TNFα were subjected to two-step ChIP assay for Groβ or TNFAIP3/A20 (39). Here, specific RelA binding was observed in unstimulated cells (compare RelA immunoprecipitate to IgG control), and relative RelA binding to Gro-β increased to 3.5-fold in response to TNFα. A weak nonspecific reduction of TNFα-induced RelA was observed in response to P028A1, whereas a greater, significant inhibitory effect of P028F4 was observed in response to TNFα (FIG. 4B, top). Similar results were observed for the TNFAIP/3A20 promoter, where the 3.5-fold increase in RelA binding was reduced to less than 2-fold (FIG. 4B, bottom). Together these data indicated that P028F4 competes for RelA binding to its endogenous chromatin binding sites, explaining its inhibitory activity.

Figure 5A:
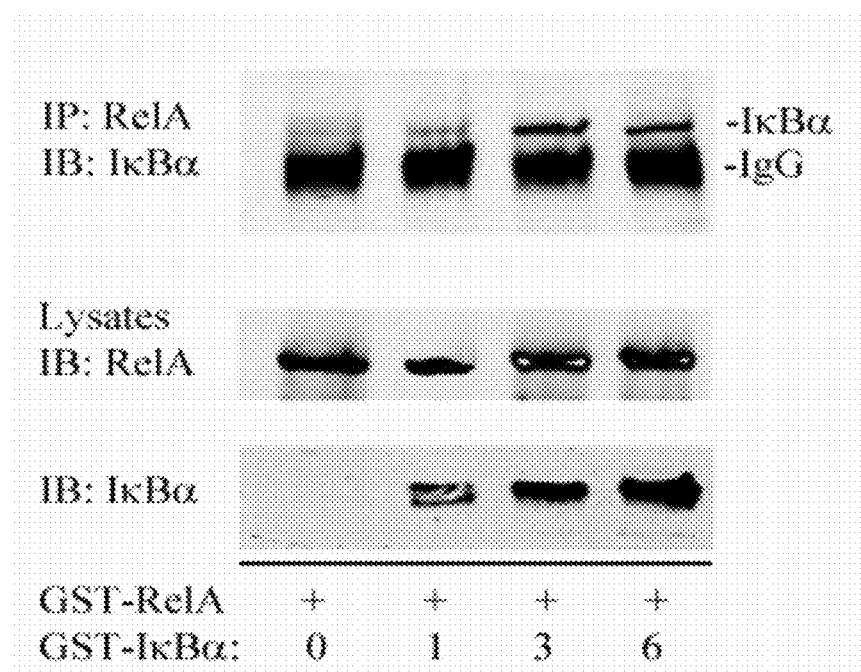
FIGS. 5A and 5B show that P028F4 binds free—but not IκBα-associated RelA: (5A) Formation of RelA·IκBα complex. Purified recombinant GST-RelA (1-313) was incubated in the absence or presence of increasing amounts of recombinant full length GST-IκBα. Complex formation was determined by nondenaturing coimmunoprecipitation using anti-RelA Ab. Top panel, immune complexes were SDS-PAGE fractionated and immunoblotted (IB) with anti-IκBα Specific IκBα band is indicated. Bottom panels are input proteins detected with anti-RelA or -IκBα Abs, (5B) EMSA of aptamer P028F4 binding to RelA and RelA·IκBα complexes. RelA. IκBα complexes were formed as described in panel A. Subsequently, radiolabeled P028F4 was added and EMSA performed. Shown is an autoradiogram of the bound and free complexes. Note the presence of P028F4·GST-RelA complex is formed only in the absence of IκBα.
Figure 5B:
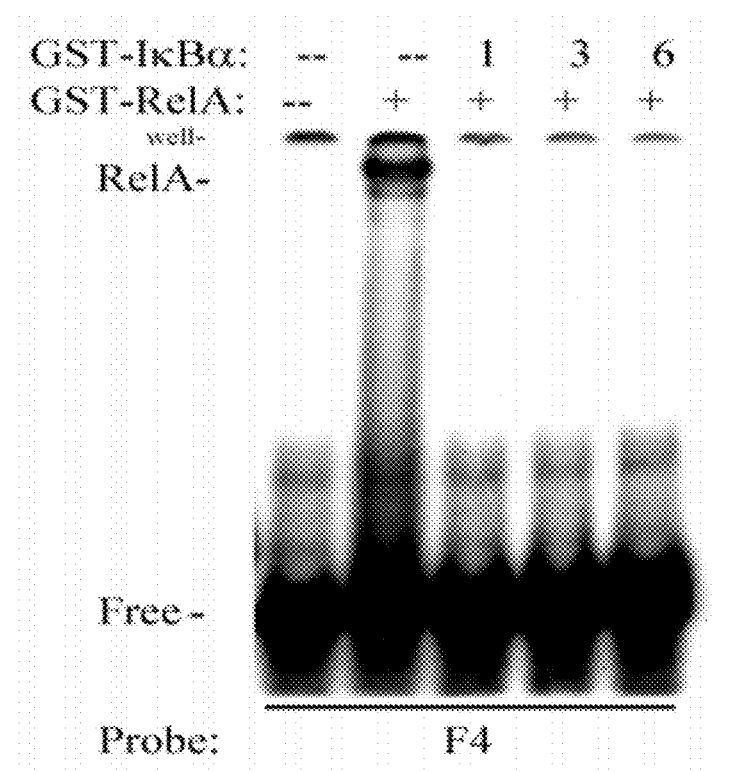

Aptamer P028F4 binds free—but not IκBα-associated RelA: IκBα binding to the $NH_2$ terminus of RelA locks it into a closed conformation for DNA binding and masks its nuclear localization sequence. To determine if P028F4 recognizes free RelA or that complexed to IκBα, purified recombinant GST-RelA (1-313) was pre-incubated in the absence or presence of increasing amounts of recombinant full length GST-IκBα. Complex formation was determined by nondenaturing coimmunoprecipitation assay using anti-RelA Ab. In this study, RelA was immunoprecipitated under native conditions, and associated IκBα detected by Western immunoblot (FIG. 5A). IκBα staining in the immunoprecipitated material indicated RelA association with IκBα. The same free RelA and RelA·κBα complex mixtures were then separately mixed with radiolabeled P028F4 for binding assay in EMSA. Although P028F4 bound to free RelA, no binding was observed for the RelA·IκBα complexes (FIG. 5B). Together, these data indicated P028F4 recognized RelA only in its activated (non IκBα-complexed) form.

Figure 6A:
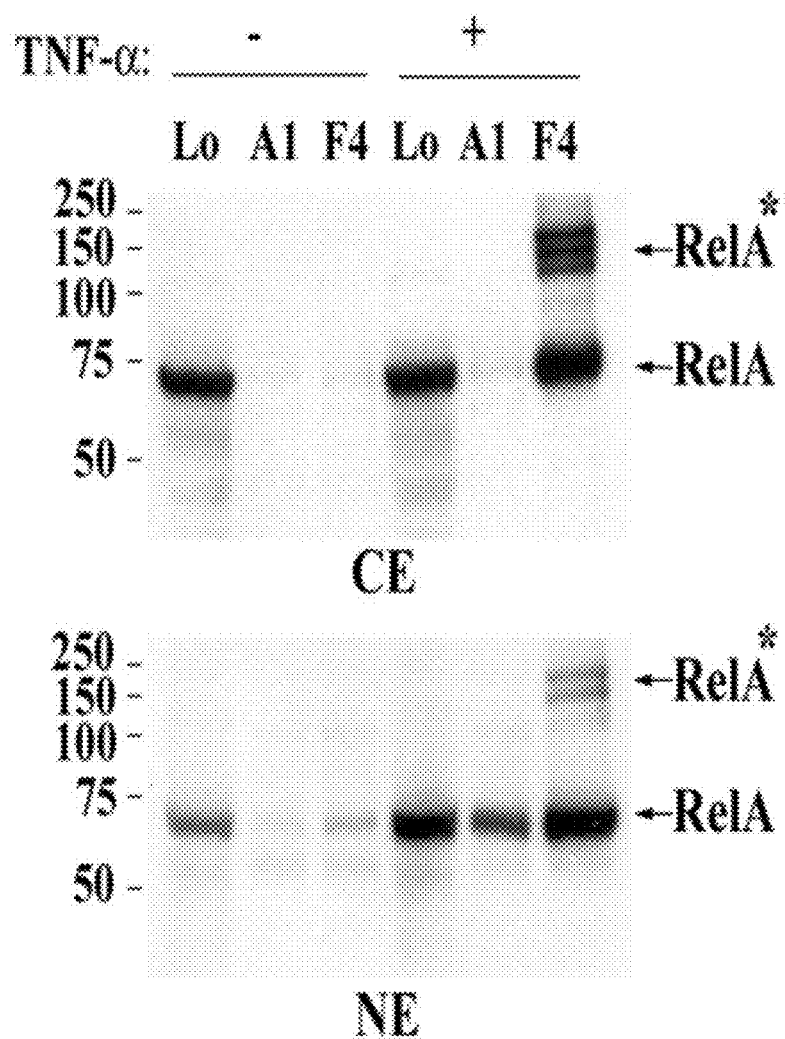
FIGS. 6A and 6B show P028F4 in tandem affinity isolation of activated RelA complexes: (6A) A549 cells were treated without TNFα (−) or with TNFα (+) for 30 min and equal amount of cytoplasmic (CE) or nuclear (NE) extracts were incubated with Bt-P028A1 or Bt-P028F4 (20 nM). Proteins bound to aptamers were captured with SA-magnetic beads and analyzed on 10% PAGE. Upper, membrane containing CE and lower, containing NE were probed with anti-RelA antibody. Arrowhead on the right indicates RelA. RelA*, post-translationally modified RelA; Lo, Sample input. Molecular weight (kDa) is indicated on the left. Study was repeated three times and (6B) Aptamer-TAP with biotinylated (Bt)-P028F4 purification was performed on EGFP-RelA WCE. Shown are fractions from the 3× peptide elution (Load), the column flow-through (Sup) and the bound fraction. Top panel, staining with anti-phospho-Ser 536 RelA Ab. The 96 kDa EGFP-RelA and endogenous 65 kDa RelA bands are indicated. Second from top, staining with anti-RelA Ab. Third from top, staining with anti-p300 coactivator Ab. Bottom panel, staining with anti-IκBα Ab. Bt, biotinylated; Lo, loaded input; IB, immunoblot; Sup, supernatant. Note that the Bound fraction is enriched in p300 and negatively selects for IκBα.

Aptamer-TAP (ATAP) purification enriches for IκBα-free RelA complexes: The ability of P028F4 to recognize non IκBα-associated RelA indicated that it could be used in affinity binding studies to selectively enrich for activated RelA complexes. For this purpose, CE or NE from control- or TNFα-stimulated A549 cells were bound to Bt-P028A1 or Bt-P028F4. After capture on SA-magnetic beads and washing, the presence of RelA was measured by Western immunoblot. In CE, it was observed that P028F4 only captured RelA prepared from TNFα-stimulated cells, whereas P028A1 did not (FIG. 6A). Although P028A1 captured nuclear RelA in TNFα stimulated cells, Bt-P028F4 captured significantly more activated RelA. In both CE and NE, aberrantly migrating forms of RelA were also captured by P028F4, suggesting that the P028F4 enriches for post-translationally modified RelA isoforms (indicated by *, FIG. 6A). These complexes are highly suggestive of inducible RelA-ubiquitin polymers shown previously to migrate at ~150 kDa (41).

Figure 6B:
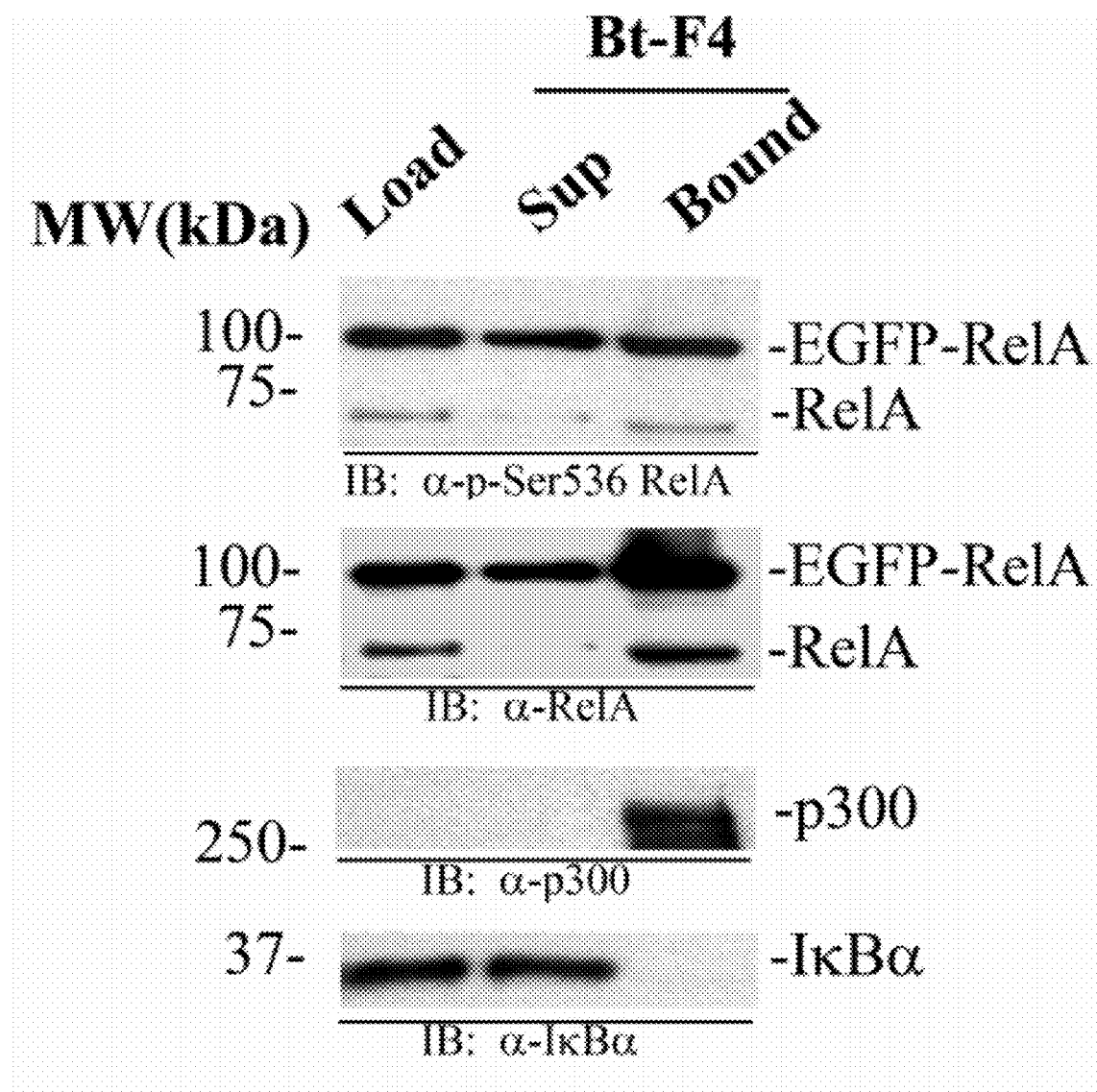

The present inventors specifically assayed whether P028F4-captured RelA was in an activated state by measurement of activating Ser 536 phosphorylation and p300 complex formation. For this purpose, a two-step affinity isolation was performed, initially purifying EGFP-RelA using FLAG-M2 affinity beads, followed by Bt-P028F4 enrichment on SA-Magnetic Beads. Western immunoblot staining with anti-phospho-Ser 536 RelA Ab shows the presence of Ser 536-phosphorylated EGFP-RelA and endogenous phospho-Ser 536 RelA in the P028F4 eluates (FIG. 6B). The abundance of p300 was below the limit of detection in the FLAG eluates, but was strongly detected in the P028F4 eluate (FIG. 6B). Finally, the inventors also monitored for IκBα association. Although IκBα was present in the starting material, IκBα was found only in the flow-through fraction (FIG. 6B, bottom panel). These data indicate that the ATAP technique enriches for a subset of RelA complexes containing activating RelA Ser phosphorylation, and p300 complexes but not inactive RelA·IκBα complexes.

The present inventors further developed quantitative measurements for the P028F4-enriched RelA and its complexes using selective reaction monitoring (SRM)-MS. First, the SRM-MS assays were optimized by selecting high responding Q1/Q3 transitions, and specificity established.

Figure 7:
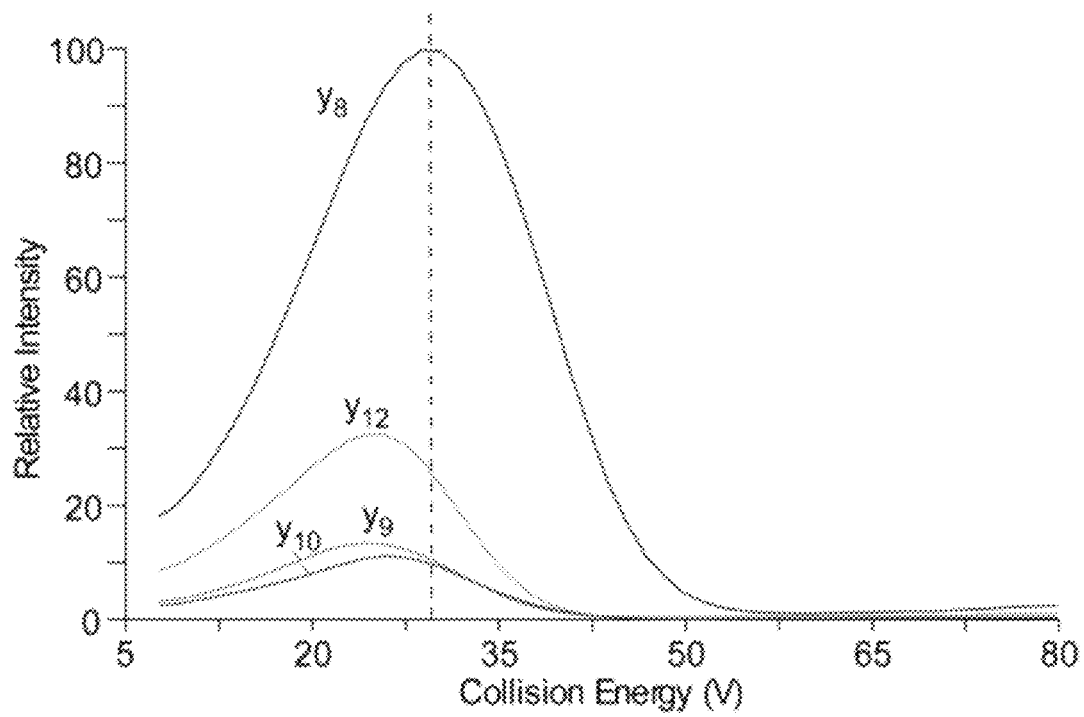
FIG. 7 shows the optimization of collision energy (CE) of precursor-product ion transitions of RelA signature peptide. A solution of SIS peptide of RelA, TPPYADPSLQAPVR (SEQ ID NO: 6) was nanoinfused to TSQ mass spectrometer, and the optimal collision energy for each transition were obtained by performing a breakdown curve. The vertical dashed lines represent the calculated CE voltage using a generic formula (CE=0.034×(precursor ion m/z)+3.314). Experimentally derived collision energies give increased sensitivity over those determined by the generic formula.

Selection and optimization of SRM Q1/Q3 transitions: Because the intensities of individual fragments derived from one precursor ion differ substantially, selection of the most intense fragments for each signature peptide is essential for developing a high-sensitivity SRM assay. In this study, four or five y-ions were selected for each peptide. The y-ions were preferred over b-ions because b-ions were usually less prominent or absent in the QQQ-MS instrument MS-MS spectra; only the y-ions whose m/z values exceed precursor ion m/z were chosen. The selection of fragment ions were on the basis of MS-MS spectra of the peptide from previous LC-MS-MS and SRM-triggered MS-MS experiments, the highest intensity fragment ions in MS-MS were selected to maximize the sensitivity of detection. The sensitivity of the SRM assays for each target peptide was further increased by optimizing collision energy. As shown in FIG. 7, the SIS RelA peptide, TPPYADPSLQAPVR (SEQ ID NO: 6) was nanoinfused into the TSQ mass spectrometer, and the optimal collision energy for each transition obtained by performing a breakdown curve. Compared to the CE voltage predicted by the generic formula $CE=0.034\times(precursor\ ion\ m/z)+3.314$, the optimized CE voltage yields slightly better results. The inventors empirically optimized the S-lens voltage for each signature peptide. The difference between the values in S-lens table generated during MS calibration and empirically derived S-lens value was found to be an average gain of less than 5% of total peak area. Therefore, in this study, we used the values in S-lens table generated during MS calibration for all the experiments. The selected Q1/Q3 transitions and their CE are tabulated in Table 1.

Figure 8:
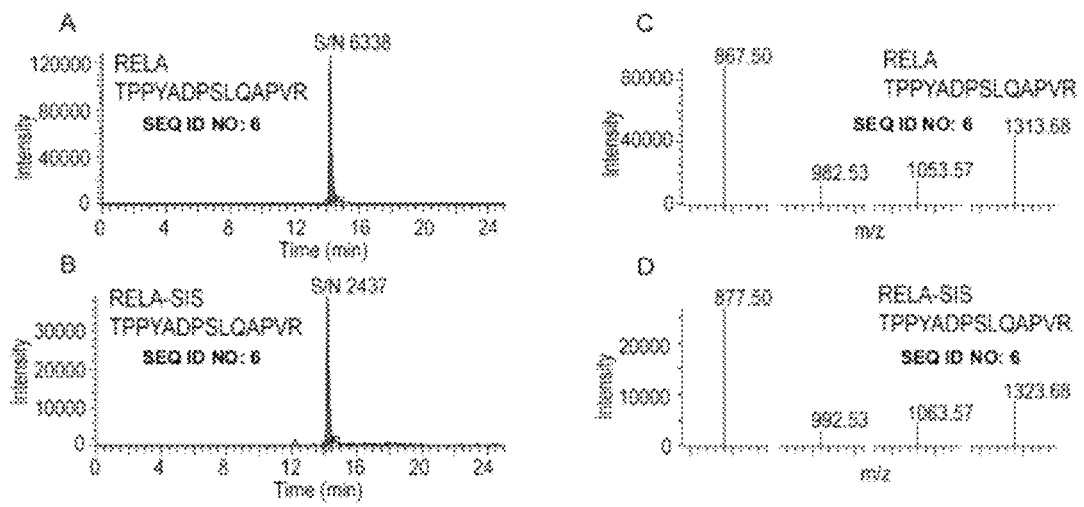
FIG. 8 shows RelA transitions. Extracted ion chromatograms (A, B) and SRM spectra (C,D) of RelA transitions monitored by SID-SRM-MS for the indicated RelA and RelA SIS peptides. It is to be noted that the SIS peptide has identical retention times (A,B), and SRM spectra (C,D) as that of the analyte.

Specificity of SRM Quantification: Shared precursor-product ion transitions with those from other analytes can lead to false positives in the subsequent peak assignment and quantification inaccuracy. With the use of SIS peptides as internal standards, we used four analyte-specific criteria-precursor ion m/z, product ion m/z, chromatographic retention time and the relative product ion intensities, for identifying chromatographic peaks that correspond to the authentic analyte peptide. Analyte peptides and their SIS analogs have identical chromatographic retention time because of their physiochemical similarities. Under the same collision energy and collision-activated dissociation pressure, the analyte and the SIS peptide dissociate to generate the same pattern of product ions, which differ only by y m/z (reflecting addition of the stable isotope-labeled amino acids) and absolute intensity. Importantly, the relative intensities of the complement of product ions formed by each analyte peptide and its SIS analog are nearly identical. These features were used for evaluating the selectivity of SRM assays and the certainty of peak assignment. For this purpose, the present inventors chose 4-5 SRM pairs for each peptide, and manually examined the MS raw data to ensure that the analyte peptides and their SIS analogs had same chromatographic retention time (variance below 0.05 min) and relative product ion intensities (±20% variance in the relative ratios for each fragment). This inspection ensured that selected SRM ion pairs of both analyte peptides and SIS peptides were free of matrix interference from co-eluting ions. As shown in FIG. 8, RelA natural peptides had nearly identical chromatographic retention time and relative product ion intensities as their SIS analogs, indicating that the SRM assays had high specificity. We believe that the high specificity of the assay was achieved, in part, because the aptamer enrichment significantly reduces the sample complexity and our application of h-SRM mode for data acquisition. Therefore, for quantification of each peptide, we used the sum of the signals from all monitored transitions instead of selecting a single representative SRM ion pair for each peptide.

Linear Response and limit of SRM Quantification of RelA: The assay dynamic range, representing the concentration range between the lower to upper limits of quantification (LLOQ to ULOQ), is the range where protein concentration is measurable with acceptable levels of accuracy and precision. The assay dynamic range was assessed by the method of standard addition (42-44). In this method, serial dilutions of target proteins with a fixed amount of SIS peptide are spiked into the similar matrix to the neat specimen, and a response calibration curve is generated for each [$^{12}$C]-analyte peptide. However, because a blank sample matrix devoid of activated endogenous RelA and a purified form of activated endogenous RelA protein are not available, we alternatively used a [$^{12}$C]-analyte peptide of RelA with its native flanking sequences (VFR-TPPYADPSLQAPVR-VSM) (SEQ ID NO: 19), to characterize the assay dynamic range. The [$^{12}$C]-analyte peptide was digested with trypsin in the same matrix as used for the "on-beads" digestion of aptamer-enriched RelA. We diluted the tryptic digest to generate a range of analyte concentrations spanning a 10,000-fold concentration range (from 200 amol to 20 pmol on the column). These analyte concentrations were then combined with a constant amount of [$^{13}$C]-analyte peptide internal standard. Two replicate LC-SRM-MS analyses of each sample dilution were performed in the order from the most dilute to the most concentrated. Linear regression analysis was performed on the observed peak area ratios (natural:heavy) vs concentration ratios to generate calibration curves (FIG. 9). The SRM assay yields linear responses over a >1,000-fold concentration range with a strong linear correlations (r>0.9971). When the amount of RelA peptide loaded on the column was higher than 10 pmol or lower than 500 amol, the response became nonlinear. The non-linearity on the high concentration is due to the saturation of both the MS detector and the nano HPLC column, whereas the non-linearity on the low concentration end is mainly because of matrix interference and the trace amount of [$^{12}$C]-analyte peptide of RelA contaminating the [$^{13}$C]-analyte peptide internal standard.

The lower limit of quantification (LLOQ) of SRM assay, the lowest analyte quantity that can be accurately measured, is the measurement of the sensitivity of the assay. The LLOQ of the SRM assay can be defined as the lowest analyte concentration that can be measured with <20% CV (45,46). In the present study, the lowest natural RelA peptide can be quantified is 200 amol (S/N 85, 10.2% CV), a value representing the LLOQ of the RelA SRM assay.

Aptamer enrichment increases signal-to-noise (S/N) ratio for RelA quantification: Using RelA-specific P028F4 to affinity enrich RelA prior to SRM-MS analysis dramatically reduces the sample complexity. To determine its effect on S/N, the inventors measured S/N for endogenous RelA in crude and P028F4-enriched samples. It was found that the S/N ratio of endogenous RelA is only 12 when analyzed directly from crude CE (FIG. 10), whereas P028F4 enrichment resulted in 36-fold increase in S/N ratio (from 12 to 429, FIG. 10).

Figure 11:
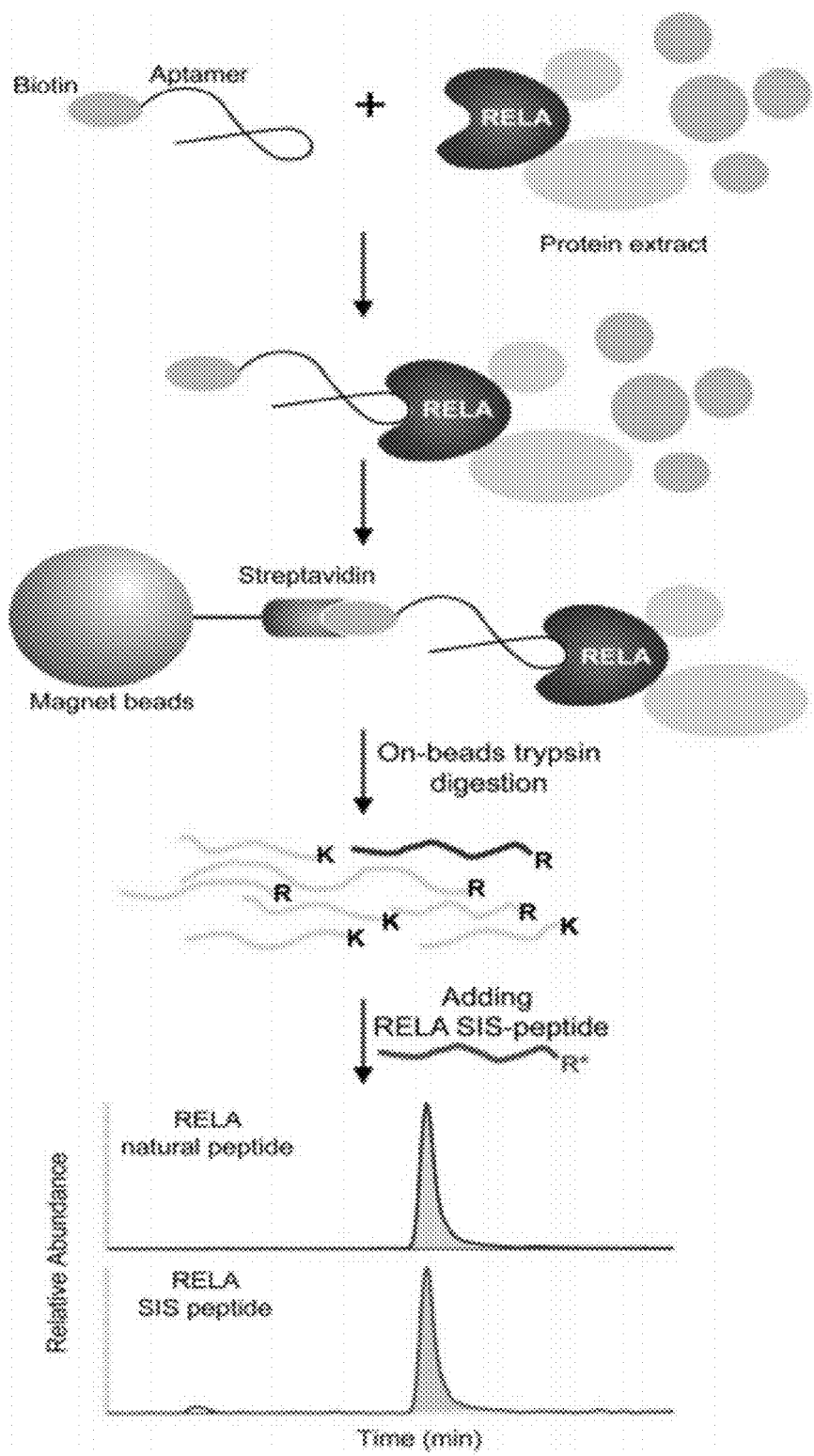
FIG. 11 is a schematic diagram of the SRM assay of aptamer-enriched RelA and its associated proteins. First, biotin-conjugated RelA specific aptamer was incubated with crude cell extract. Secondly, the Bt-aptamer RelA was captured by SA-coated magnetic beads. The beads were washed 6 times to remove non-specifically bound proteins. The washing improved the purity of isolated RelA and reduced the complexity of the sample. Third, the beads were resuspended in trypsin proteolysis buffer and the proteins bound on the beads were digested with trypsin. Fourth, the tryptic peptides were eluted from the beads and the SIS standard peptides were spiked before SID-SRM-MS analysis. Finally, RelA was quantified with SID-SRM-MS.
Figure 12A:
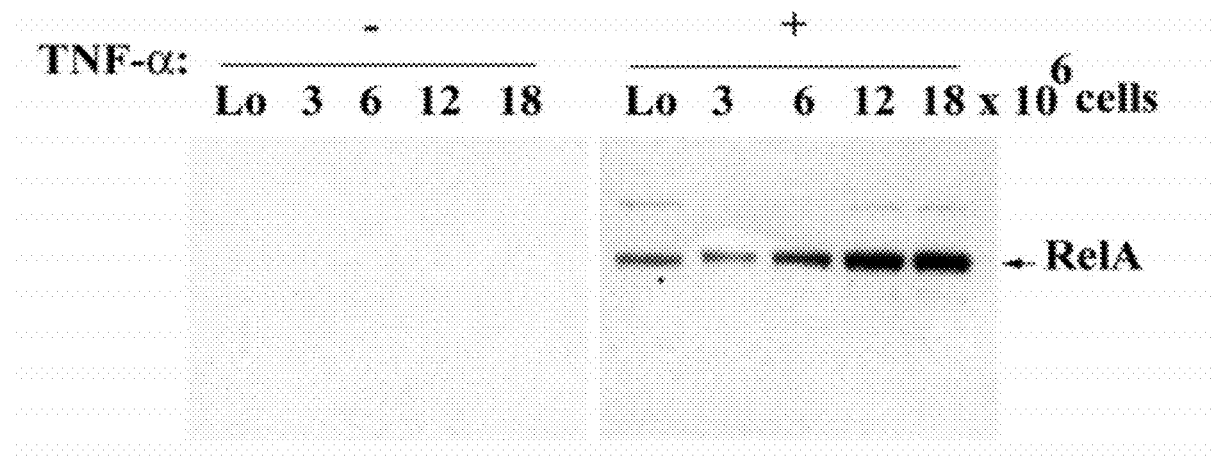
FIGS. 12A and 12B show a single step isolation of endogenous RelA: (12A) RelA binding with P028F4 with increasing amounts of nuclear extracts from A549 cells. Left, nuclear extracts from indicated cell number without TNFα (−) and right, with TNFα (+) were captured with P028F4 and bound complexes quantified by Western immunoblot. Arrowhead indicated RelA detected by Western blot with anti-RelA antibody, (12B) Quantitation of bound RelA to Bt-P028F4 by Odyssey infrared scanning.
Figure 12B:
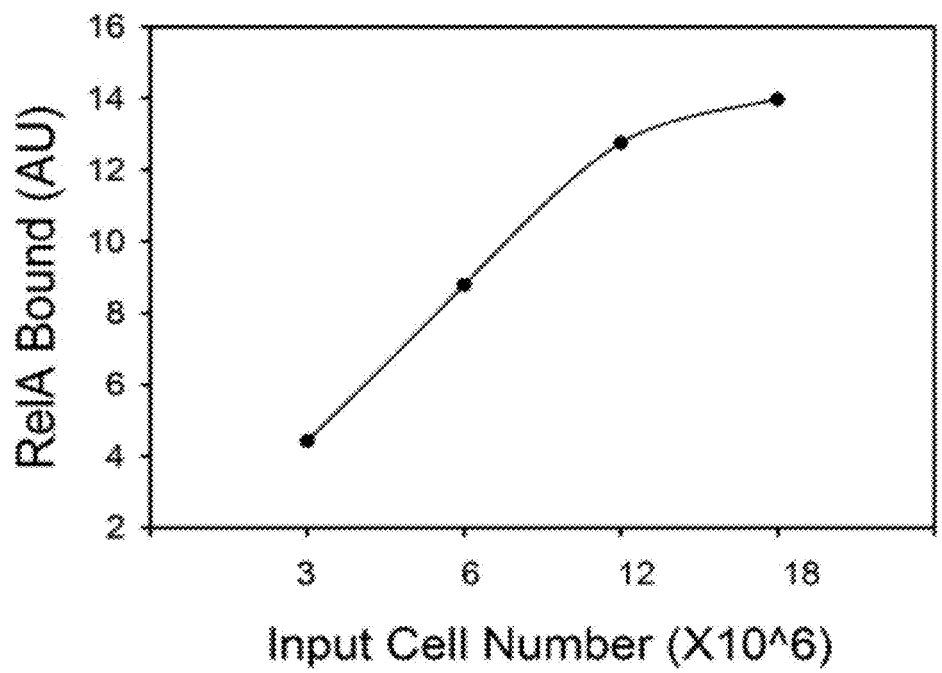

Multiplexed LC-SRM-MS analysis of single-step aptamer-enriched RelA: The present inventors combined single-step aptamer-enrichment of RelA in eukaryotic cells with the multiplex SRM assay (schematically shown in FIG. 11). Control or TNFα-stimulated A549 cells were fractionated into CE or NE fractions, incubated with Bt-P028F4 or P028A1 aptamers, and captured on SA-magnetic beads. To first determine whether the aptamer capture on SA-magnetic beads was non-saturating, RelA from increasing numbers of control- or TNFα-stimulated A549 cells were subjected to single-step aptamer enrichment, and detected by Western immunoblot. As seen in FIGS. 12A and 12B, increasing amounts of RelA were seen over the input range of 3-12×10$^6$ cells only in the TNF-stimulated extracts.

Figure 13A:
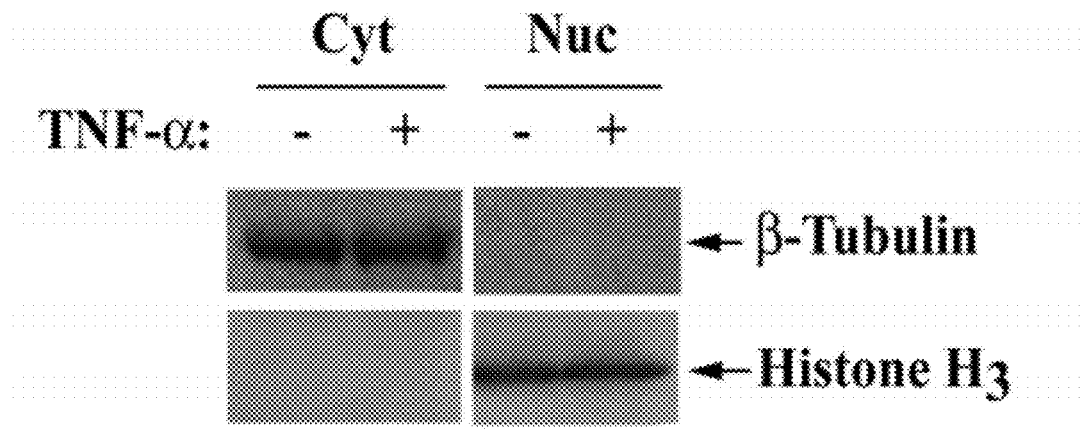
FIGS. 13A and 13B show the SID-SRM-MS quantification of total and activated RelA in A549 cells: (13A) Assessment of cytoplasmic and nuclear fractionation. Western immunoblot for β-tubulin and histone H3 and (12B) cytoplasmic fraction without TNFα stimulation; (B), RelA quantification after single step aptamer enrichment for control or TNFα stimulated CE (top) or NE (bottom). The error bars indicate S.D. of the measurements.
Figure 13B:
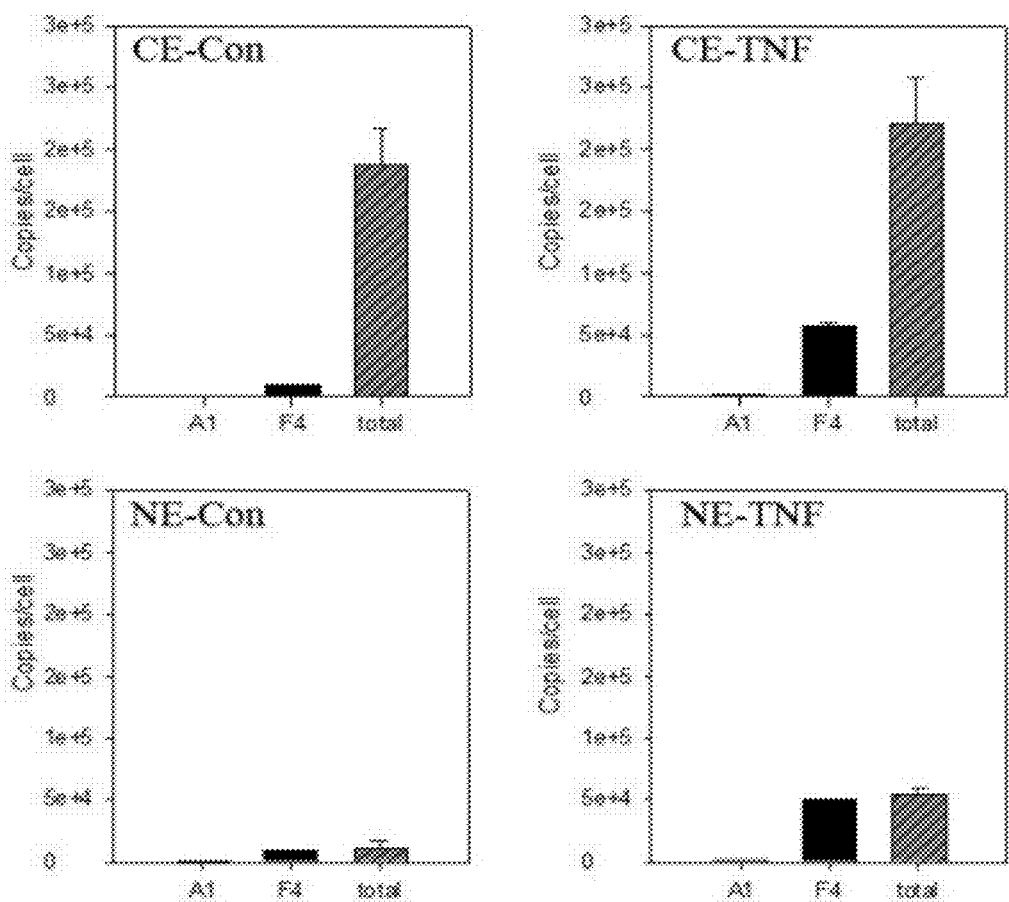

To quantify the amount of RelA in cells, CE and NE from 6×10$^6$ cells were prepared and assayed for cytoplasmic and nuclear markers. As seen in FIG. 13A, CE were highly enriched in β-tubulin, whereas β-tubulin was undetectable in NE. Similarly, histone H3 was undetectable in CE and highly enriched in NE. The active RelA in CE and NE were then captured by Bt-aptamer-SA magnetic beads. The proteins were trypsinized on-beads, and RelA and IκBα were quantified with SID-SRM-MS. To determine the fraction of activated RelA complex, total RelA in each subcellular extract was also quantified with SID-SRM-MS. As shown in FIG. 13B, P028F4 demonstrated high specificity toward activated RelA in comparison to P028A1, resulting in 14-30 fold enrichment of activated RelA in CE and NE. With the quantification of SID-SRM-MS, the inventors found that, in unstimulated cells, about 5% of total RelA proteins in the cytoplasm were activated, and only a small amount of activated (and total) RelA was in the nucleus. By contrast, after TNFα stimulation, the amount of activated RelA in CE increased about 6-fold. The inventors also observed a significant amount of activated RelA translocated into the nucleus, where the amount of activated RelA was the same as the total amount of nuclear RelA. Although it was measured, IκBα was not observed in any of the aptamer-enriched samples, a finding that is consistent with the lack of RelA-IκBα complex binding seen in Western blot analysis (FIG. 6B), and in EMSA (FIG. 5).

In addition to P028F4, the present inventors also describe other aptamers that bind to NFκB/RelA. The sequences of these aptamers are presented in Table 3 herein below.

Mucosal inflammation produced by the innate immune response is dependent on the NF-κB pathway, an intracellular signaling network whose activity is regulated by the formation of dynamic protein interactions. Activated pattern recognition- or cytokine receptors binding to their cognate ligands induce Lys 63 linked polyuquitiylation of the RIP and TRAF adapter molecules (6). These polyubiquityl-modified adapters recruit IKK to the submembranous receptor complex, producing serine phosphorylation and activation of IKK, an event that controls protein stability of IκBα and nuclear translocation of activated RelA. In the nucleus, RelA associates with the p300 histone acetyltransferase, whose promoter recruitment activates expression of downstream inflammatory genetic networks. As a result of direct activation of negative feedback networks including IκBα synthesis, RelA undergoes nuclear-cytoplasmic oscillation in response to activation (47). In this study, the inventors describe the selection and characterization of a RelA-directed ssDNA oligonucleotide, P028F4, a ligand that directly binds recombinant RelA in vitro, and binds inducible RelA in isolated NEs.

P028F4 enriches for serine phosphorylated and p300-complexed RelA. The inventors provide evidence that P028F4 has utility as a method for single step enrichment and quantification of activated RelA complexes using quantitative SID-SRM-MS assays. This method has, for the first time, allowed the determination of the fraction of activated RelA in unstimulated cells and the estimation of activated RelA molecules.

TABLE 3

Aptamers to NFκB/RelA.

| Aptamer | Sequence | SEQ ID NO: |
|---|---|---|
| *Group I* | | |
| P028F4 | GGGTAACCTTGAGTCACGAATTCAAGCGGGACAGGAGAAACACGG CATGTCAGCGAAGGTACCCAACTTACAGCTTCTGG | 9 |
| P028F5 | GGGTAACCTTGAGTCACGAATTCAATAGCGGGCCAGGATGGAAGG TATGGCAGCGAAGGTACCCAACTTACAGCTTCTGG | 10 |
| P026H5 | CTTTGGTCAGCCTCTAATGGCTCGTGGGACAGTGTGTGTTCAGTCA AACGTGGC TGGCTCTCCAAGAATCCCCGTAGTT | 11 |
| P026G2 | CTTTGGTCAGCCTCTAATGGCTCGTGGCAGGAACGGGCCTTAGCTT GGCATTGGGTGGCTCTCCAAGAATCCCCGTAGTT | 12 |
| P026H12 | CTTTGGTCAGCCTCTAATGGCTCGTGGGACAGGAGGTACGGAATGT CAGCGAACGTGGCTCTCCAAGAATCCCCGTAGTT | 13 |
| *Group II* | | |
| P028E8 | GGGTAACCTTGAGTCACGAATTCAAGCAGTTCCCACTGACCTTAAA TTCTGCACCAAGGTACCCAACTTACAGCTTCTGG | 14 |
| P028F10 | GGGTAACCTTGAGTCACGAATTCAACCACTCCTATTCACACTATCC CCTTTCCCGAAGGTACCCAACTTACAGCTTCTGG | 15 |
| P028F12 | GGGTAACCTTGAGTCACGAATTCAACCACAAAATCGTGCCGTTCAA TATCTGACCAAGGTACCCAACTTACAGCTTCTGG | 16 |
| P026F12 | CTTTGGTCAGCCTCTAATGGCTCGTGGGGAGCACACGCATTGGTAC CGTCTGGTATGGCTCTCCAAGAATCCCCGTAGTT | 17 |

Competition studies on the aptamers described in Table 3 showed that the aptamers in Group I competed for RelA binding with each other. Aptamers in Group II do not compete with Group I aptamers. Bolding indicates the binding specific variable regions of the aptamers. The flanking sequences are the PCR primer binding sites required for amplification of the aptamers. Genetic selection of protein-binding aptamers is a widely exploited method for probing protein function and structure (20,21). Previous efforts isolating RelA ligands have resulted in isolation of ssRNA aptamers and ds-thioate- and dithioate modified ligands that bind NF-κB/RelA (48, 49). To our knowledge, this work represents the first report of isolation of a ssDNA aptamer that specifically recognizes NF-κB/RelA. Our data show that P028F4 binds with a $K_D$ of $6.4 \times 10^{-10}$ M, representing about 10-fold higher affinity than that of the reported ssRNA aptamers (48). Moreover, this binding is more stable than that described for duplex DNA binding to RelA. Although previous work showing that thioate modified duplex aptamers can recognize specific NF-κB isoforms, their on and off-rates have not been reported (49). One property of P028F4 is that this ligand binds with a long off-rate, measured by SPR with a $k_d$ of 0.0018 l/s. This characteristic lends itself well to its application for affinity isolations of the target protein and its complexes.

The crystallographic structure of the RelA-complexed to its duplex binding sites shows that RelA binds as a dimer, assuming an immunoglobulin fold structure with β-stranded loops making extensive contract with both DNA base pairs and the sugar-phosphate backbone (50). The binding characterization described herein shows that ssDNA P028F4 competes with RelA for its cognate dsDNA regulatory sequences. These data may suggest that P028F4 binds RelA on a β-stranded loop that is essential for stable DNA binding, or alternatively, P028F4 may induce RelA to assume a conformational change nonpermissive for DNA interaction. In this regard, it is to be noted that a high affinity ssRNA aptamer that selectively binds NF-κB p50 isoform also competes with duplex DNA binding by inducing an alternative molecular conformation of the protein (51).

Because P028F4 is a competitive antagonist of activated RelA DNA binding activity, the inventors explored its properties as antagonist of RelA transcriptional activity in intact cells. Although we observed that cellular transfection of P028F4 produced additional inhibition of expression of NF-κB dependent target genes over that of the control P028A1 aptamer, the studies herein also indicate that at the concentrations needed to overcome nonspecific cellular binding (29), there is a non-specific aptamer effect on TNFα-inducible transcription (FIG. 4A). In the ChIP studies, an even stronger non-specific aptamer effect was also seen (FIG. 4B). We ascribe these nonspecific P028A1 effects as being due to well-recognized low affinity interactions of cellular transcription factors for nonspecific DNA, and is consistent with its weak abilities to compete for RelA binding in nitrocellulose filter binding assays (Table 2), and capture RelA in aptamer-affinity binding studies (FIG. 6A). This nonspecific effect will need to be reduced before ssDNA aptamers like P028F4 can be used to modify RelA action in intact cells.

An important feature of P028F4-RelA interaction, exploited in this study, is that IκBα-complexed RelA is not recognized by P028F4. The inventors base this conclusion on the inability of P028F4 to bind to purified recombinant IκBα-complexed RelA (FIG. 5), its colocalization with activated EGFP-RelA in isolated nuclei (FIG. 3A), its binding to post-translationally modified RelA in cellular extracts (FIG. 6B), and its binding enrichment of RelA (over that of IκBα) in affinity isolations measured by quantitative SRM-MS assays. Previous work has shown that IκBα binds the NH2 terminus of RelA with a 1:1 stoichiometry on discontinuous sequences through its 7 ankryin repeat domains. X-Ray crystallographic analysis of the IκBα·RelA complex shows that first two ankryin repeats bind (and mask) the RelA nuclear localization signal, and the sixth repeat occludes the RelA DNA-binding cleft (52). Through these interactions, IκBα is able to both inhibit RelA nuclear translocation as well as its DNA binding activity.

Although DNA aptamers have been used as affinity reagents for identifying biomarkers in complex fluids (53), they have not yet been fully exploited in protein quantification. The approach demonstrated herein combines aptamer-enrichment of RelA and SRM-MS quantification using stable isotopic dilution methods. Compared to direct quantification of RelA and associated proteins from crude cell extracts, aptamer-based enrichment approach has several advantages. First, using a RelA-specific aptamer to enrich RelA and its associated proteins prior to SRM-MS analysis dramatically reduces the sample complexity and hence improves the S/N ratio of endogenous RelA 36-fold. Second, aptamer enrichment also reduces the likelyhood of the interference of other analytes, which have isobaric (or very similar m/z values) to the target peptides. Therefore the specificity and accuracy of SRM assay are significantly improved. Third, aptamer enrichment allows RelA to be isolated from a large amount of protein extract so that the amount of endogenous RelA peptide falls in the middle of linear dynamic range of the calibration curve, which improves the accuracy and reproducibility of quantification. This feature is especially attractive for quantification of low-abundance proteins, such as RelA or p300 transcription factors, in complex protein mixtures. Finally, because P028F4 selectively recognizes the IκBα-free, activated form of RelA, we are able to quantify the abundance of the activated form of RelA. This measurement cannot be accomplished by directly analyzing RelA abundance in crude cellular (or subcellular) extracts.

Described earlier, RelA is a cytoplasmic transcription factor that undergoes constitutive nuclear-cytoplasmic transport. In the unstimulated cell, RelA is sequestered in the cytoplasm predominately by binding the IκBα inhibitor, an association that masks the nuclear localization sequence, shifting the nuclear-cytoplasmic equilibrium of RelA to the cytoplasmic compartment. Stimulus-induced RelA activation is mediated by IκBα proteolysis, liberating a fraction of sequestered RelA to translocate into the nucleus, shifting the equilibrium to the nuclear compartment. The theoretical understanding of NF-κB regulation has been developed using computational modeling approaches, where the relative contributions of the IκB isoforms and the effect of the negative feedback loops have been inferred (54,55). Despite this understanding of pathway connections, the dynamics of negative feedback loops are dependent on the fraction of activated RelA that enters the nucleus. This value is based on assumed values because the precise concentration of activated RelA has not yet been experimentally determined.

The present invention represents the first quantitative estimate of the number of activated RelA molecules. In a recent study, using single-cell dynamic imaging and quantitative Western blot measurements, the inventors observed that only a small fraction of total cytoplasmic RelA is induced to translocate into the nucleus, introducing the concept of an inert, cytoplasmic RelA reservoir (56). When parameters describing the RelA cytoplasmic reservoir are incorporated into the deterministic model, Bayesian inference estimation for the number of RelA molecules that translocate approximates 10-20% of the total cytoplasmic amount. Using this correction, the ability of the model to predict biologically relevant behavior improved significantly (56). However, the exact component of activated RelA has only been assumed in these models.

The aptamer-SID-SRM estimation of 200,000 total molecules of RelA/cell with 50,000 molecules/cell of activated RelA in the nucleus after TNFα stimulation are in good agreement with our previous quantitative Western blot studies (56). It is also to be noted that the amount of activated RelA is equivalent with the amount of total RelA in both control and TNFα stimulated NE. The findings described herein indicate that the majority of RelA present in the NE is in the activated state, consistent with the previous findings by the present inventors using Western immunoblots that the amount of nuclear IκBα is very low. The estimate the present inventors make here for the number of activated RelA molecules in CE has not yet been possible without the development of P028F4, and its ability to discriminate between the bound—and free RelA fractions. It is interesting to note that the number of copies of activated RelA in CE and NE in stimulated cells are similar—a finding that may have implications in understanding the energetics controlling nuclear RelA import The NF-κB/RelA aptamers of the present invention can be utilized for imaging the anatomical sites or extent of inflammation in a number of disease states. The, NF-κB/RelA aptamers described herein can be synthesized as synthetic conjugates to contrast agents that will localize to specific sites of inflammation. Imaging modalities can include ultrasound (US), or magnetic resonance (MR) imaging. For example, NF-κB/RelA aptamers can be conjugated to microbubbles; injection of NF-κB/RelA-microbubbles will allow the detection of the site or amount of inflammation in the cardiovascular system by high resolution ultrasonography. Similarly conjugation of NFkB/RelA aptamers to gadolinium-DTPA producing a paramagnetic liposome. Intravenous injection of the conjugate will result in localization and allow the detection of inflammation by MR imaging.

Imaging using NF-κB/RelA conjugated to contrast agents can be used to assess the presence, location, or extent of inflammation in human inflammatory diseases. These diseases would include asthma, chronic obstructive lung disease, inflammatory bowel disease, cardiovascular disease (atherosclerosis and aortic dissections) and specific cancers (prostate, melanoma) diseases whose etiology and progression are known to be mediated by NF-κB/RelA signaling (57-65). Quantification of the presence, location, or extent of inflammation in human inflammatory diseases can be used as a surrogate endpoint in clinical trials to determine the effectiveness of the drug, or assess the individual response to the therapy. Some non-limiting agents to which the aptamers of the present invention can be conjugates include radionuclides (technetium, indium, fluorine, iodine, bromine isotopes conjugated to targeting aptamers), gold (gold as a contrast agent for aptamers), magnetic nanoparticles (paramagnetic bead-aptamer conjugate used for MRI), fluorescent (Cy5 labeled aptamers used for whole-body imaging in mice), quantum dots (aptamer-quantum dot-doxorubicin conjugate for combined imaging and therapy), and gadolinium (gadolinium for imaging includes liposomes and microbubbles).

NF-κB/RelA targeted aptamers can be used to inhibit the actions of NFkB/RelA in mediating tissue inflammation (57-65) or cancer. These formulations could involve encapsulation in nanoparticles to enhance cellular uptake, and conjugation of the aptamer to anti-proliferative agents. In addition effector molecules can also be attached to the aptamers for therapeutic purposes. Non-limiting examples of the effector molecules include toxins (RNA aptamer:gelonin conjugates to kill prostate cancer cells), radionuclides (Technetium 99m conjugated aptamers to target tenascin C expressing tumor cells), nanoparticles (nanoparticle encapsulated drugs), chemotherapeutic agents (aptamers conjugated to doxorubicin, daunorubicin, cisplatin), photodynamic agents (aptamers conjugated to the photosensitizing agent chlorine e6), and gold (aptamer-gold nanoparticle-doxorubicin bioconjugate for CT imaging and scanning).

In conclusion, RelA aptamer-SID-SRM is a versatile tool for quantification of the abundance of activated protein and its complex. Aptamer enrichment enhances assay specificity, S/N ratio, and sensitivity. Further exploitation of this approach will allow for systematic extension of the dynamics of RelA activation in response to diverse ligands, and exploration of protein interaction networks of the molecule in its activated form.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

U.S. Patent Application No. 20080261225: Method and Kit for Detecting A Target Protein using A DNA Aptamer.

U.S. Pat. No. 6,867,289: Thio-Modified Aptamer Synthetic Methods and Compositions.

U.S. Pat. No. 7,309,786: Oligonucleotide Antagonist for Human Tumor Necrosis Factor α (TNF-α).

1. Brasier A. R. (2008). The NF-κB Signaling Network: Insights from systems approaches. In Cellular Signaling And Innate Immune Responses To RNA Virus Infections, Brasier A R, Lemon S M, Garcia-Sastre A, eds. American Society for Microbiology), pp. 119-135

2. Akira, S., Uematsu S., and Takeuchi O. (2006) Pathogen Recognition and Innate Immunity. Cell 124, 783-801

3. Tian, B., Nowak D. E., and Brasier A. R. (2005) A TNF-induced gene expression program under oscillatory NF-kappaB control. BMC Genomics 6, 137-154

4. Tian, B., Nowak D. E., Jamaluddin M., Wang S., and Brasier A. R. (2005) Identification of Direct Genomic Targets Downstream of the Nuclear Factor-{kappa}B Transcription Factor Mediating Tumor Necrosis Factor Signaling. Journal of Biological Chemistry 280, 17435-17448

5. Beg, A. A., Baldwin A. S. J. (1993) The I kappa B proteins: multifunctional regulators of Rel/NF-kappa B transcription factors. Genes Dev 7, 2064-2070

6. Ea, C. K., Deng L., Xia Z. P., Pineda G., and Chen Z. J. (2006) Activation of IKK by TNF[alpha] Requires Site-Specific Ubiquitination of RIP1 and Polyubiquitin Binding by NEMO. Molecular Cell 22, 245-257

7. Hsu, H., Huang J., Shu H. B., Baichwal V., and Goeddel D. V. (1996) TNF-dependent recruitment of the protein kinase RIP to the TNF receptor-1 signaling complex. Immunity 4, 387-396

8. Poyet, J.-L., Srinivasula S. M., Lin J.-H., Fernandes-Alnemri T., Yamaoka S., Tsichlis P. N., and Alnemri E. S. (2000) Activation of the IkB kinases by RIP via IKKg/NEMO-mediated oligomerization. J. Biol. Chem. 275, 37966-37977

9. Delhase, M., Hayakawa M., Chen Y., and Karin M. (1999) Positive and negative regulation of IkB kinase activity through IKKb subunit phosphorylation. Science 284, 309-313

10. Karin, M. (1999) The beginning of the end: IkappaB kinase (IKK) and NF-kappaB activation. J Biol Chem 274, 27339-27342

11. Maniatis, T. (1997) Catalysis by a multiprotein IkB kinase complex. Science 278, 818-819

12. Han, Y., Weinman S., Boldogh I., Walker R. K., and Brasier A. R. (1999) Tumor necrosis factor-alpha-inducible IkappaBalpha proteolysis mediated by cytosolic m-calpain. A mechanism parallel to the ubiquitin-proteasome pathway for nuclear factor-kappab activation. J Biol Chem. 274, 787-794

13. Jamaluddin, M., Wang S., Boldogh I., Tian B., and Brasier A. R. (2007) TNF-Induced NF-κB/Rel A Ser 276 Phosphorylation And Enhanceosome Formation On The IL-8 Promoter Is Mediated By A Reactive Oxygen Species (ROS)-Dependent Pathway. Cellular Signaling 9, 1419-1433

14. Sasaki, C. Y., Barberi T. J., Ghosh P., and Longo D. L. (2005) Phosphorylation of RelA/p65 on Serine 536 Defines an I{kappa}B{alpha}-independent NF-{kappa}B Pathway. J. Biol. Chem. 280, 34538-34547

15. Cui, R., Tieu B., Recinos A. I., Tilton R. G., and Brasier A. R. (2006) Rho A Mediates Angiotensin II-Induced Phospho-Ser536 NF-kB/RelA Subunit Exchange on the IL-6 Promoter in VSMCs. Circ Res 99, 723-730

16. Zhong, H., May M. J., Jimi E., and Ghosh S. (2002) The Phosphorylation Status of Nuclear NF-[kappa]B Determines Its Association with CBP/p300 or HDAC-1. Molecular Cell 9, 625-636

17. Chen, L. f., Williams S. A., Mu Y., Nakano H., Duerr J. M., Buckbinder L., and Greene W. C. (2005) NF-{kappa}B RelA Phosphorylation Regulates RelA Acetylation. Mol Cell Biol 25, 7966-7975

18. Puig, O., Caspary F., Rigaut G., Rutz B., Bouveret E., Bragado-Nilsson E., Wilm M., and Seraphin B. (2001) The Tandem Affinity Purification (TAP) Method: A General Procedure of Protein Complex Purification. METHODS 24, 218-229

19. Bouwmeester, T., Bauch A., Ruffner H., Angrand P. O., Bergamini G., Croughton K., Cruciat C., Eberhard D., Gagneur J., Ghidelli S., Hopf C., Huhse B., Mangano R., Michon A. M., Schirle M., Schlegl J., Schwab M., Stein M. A., Bauer A., Casari G., Drewes G., Gavin A. C., Jackson D. B., Joberty G., Neubauer G., Rick J., Kuster B., and Superti-Furga G. (2004) A physical and functional map of the human TNF-[alpha]/NF-[kappa]B signal transduction pathway. Nat Cell Biol 6, 97-105

20. Ellington, A. D., Szostak J. W. (1990) In vitro selection of RNA molecules that bind specific ligands. Nature 346, 818-822

21. Tuerk, C., Gold L. (1990) Systematic evolution of ligands by exponential enrichment: RNA ligands to bacteriophage T4 DNA polymerase. Science 249, 505-510

22. Widen, S. G., Wilson S. H. (1991) Mammalian beta-polymerase promoter: large-scale purification and properties of ATF/CREB palindrome binding protein from bovine testes. Biochemistry 30, 6296-6305

23. Jamaluddin, M., Tian B., Boldogh I., Garofalo R., and Brasier A. R. (2009) Respiratory Syncyctial Virus Infection Induces A ROS-MSK1-Phospho-Ser-276 RelA Pathway Required For Cytokine Expression. J Virol 83, 10605-10615

24. Liu, P., Lu M., Tian B., Li K., Garofalo R. P., and Brasier A. R. (2009) Expression Of An IKKγ Splice Variant Determines IRF3—Canonical NF-κB Pathway Utilization In ssRNA Virus Infection. PLoS ONE 14, e8079

25. Tian, B., Nowak D. E., and Brasier A. R. (2005) A TNF-induced gene expression program under oscillatory NF-kappaB control. BMC Genomics 6, 137-154

26. Akagi, T., Sasai K., and Hanafusa H. (2003) Refractory nature of normal human diploid fibroblasts with respect to oncogene-mediated transformation. Proceedings of the National Academy of Sciences of the United States of America 100, 13567-13572

27. Forbus, J., Spratt H., Wiktorowicz J., Wu Z., Boldogh I., Denner L., Kurosky A., Brasier R. C., Luxon B., and Brasier A. R. (2006) Functional Analysis Of The Nuclear Proteome Of Human A549 Alveolar Epithelial Cells By HPLC—High Resolution 2D Gel Electrophoresis. Proteomics 6, 2656-2672

28. Jamaluddin, M., Wiktorowicz J. E., Soman K. V., Boldogh I., Forbus J., Spratt H., Garofalo R. P., and Brasier A. R. (2010) Role of Peroxiredoxin-1 and -4 in Protection of RSV-induced Cysteinyl-oxidation of Nuclear Cytoskeletal Proteins. J Virol 84, 9533-9545

29. Stanlis, K. K. H., McIntosh J. R. (2003) Single-strand DNA Aptamers as Probes for Protein Localization in Cells. J. Histochem. Cytochem. 51, 797-808

30. Jamaluddin, M., Casola A., Garofalo R. P., Han Y., Elliott T., Ogra P. L., and Brasier A. R. (1998) The major component of IkBa proteolysis occurs independently of the proteasome pathway in Respiratory Syncytial Virus-infected pulmonary epithelial cells. J Virol 72, 4849-4857

31. Tian, B., Nowak D. E., Jamaluddin M., Wang S., and Brasier A. R. (2005) Identification of Direct Genomic Targets Downstream of the Nuclear Factor-{kappa}B Transcription Factor Mediating Tumor Necrosis Factor Signaling. J. Biol. Chem. 280, 17435-17448

32. Hou, T., Ray S., and Brasier A. R. (2007) The functional role of an IL-6 inducible CDK9-STAT3 complex in human γ-fibrinogen gene expression. J. Biol. Chem. 282, 37091-37102

33. Nowak, D. E., Tian B., and Brasier A. R. (2005) Two-Step Cross-linking method for Identification of NF-B Gene Network by Chromatin Immunoprecipitation. Biotechniques 39, 715-725

34. Tian, B., Yang J., and Brasier A. R. (2011) Two-step Crosslinking for Analysis of Protein-Chromatin Interactions. Methods in Molecular Biology in press, 35. Miceli, R. M., DeGraaf M. E., and Fischer H. D. (1994) Two-stage selection of sequences from a random phage display library delineates both core residues and permitted structural range within an epitope. Journal of Immunological Methods 167, 279-287

36. Lange, V., Picotti P., Domon B., and Aebersold R. (2008) Selected reaction monitoring for quantitative proteomics: a tutorial. Mol. Syst. Biol. 4, 222

37. Markham, N. R., Zuker M. (2008) UNAFold: software for nucleic acid folding and hybridization. Methods Mol. Biol 453, 3-31

38. Garofalo, R., Sabry M., Jamaluddin M., Yu R. K., Casola A., Ogra P. L., and Brasier A. R. (1996) Transcriptional activation of the interleukin-8 gene by RSV infection in alveolar epithelial cells: Nuclear translocation of the Rel A transcription factor as a mechanism producing airway mucosal inflammation. J Virol 70, 8773-8781

39. Nowak, D. E., Tian B., Jamaluddin M., Boldogh I., Vergara L. A., Choudhary S., and Brasier A. R. (2008) RelA Ser276 Phosphorylation Is Required for Activation of a Sub- 40. Bosisio, D., Marazzi I., Agresti A., Shimizu N., Bianchi M. E., and Natoli G. (2006) A hyper-dynamic equilibrium between promoter-bound and nucleoplasmic dimers controls NF-kappaB-dependent gene activity. EMBO J 25, 798-810

41. Thoms, H. C., Loveridge C. J., Simpson J., Clipson A., Reinhardt K., Dunlop M. G., and Stark L. A. (2010) Nucleolar Targeting of RelA(p65) Is Regulated by COMMD1-Dependent Ubiquitination. Cancer Research 70, 139-149

42. Addona, T. A., Abbatiello S. E., Schilling B., Skates S. J., Mani D. R., Bunk D. M., Spiegelman C. H., Zimmerman L. J., Ham A. J., Keshishian H., Hall S. C., Allen S., Blackman R. K., Borchers C. H., Buck C., Cardasis H. L., Cusack M. P., Dodder N. G., Gibson B. W., Held J. M., Hiltke T., Jackson A., Johansen E. B., Kinsinger C. R., Li J., Mesri M., Neubert T. A., Niles R. K., Pulsipher T. C., Ransohoff D., Rodriguez H., Rudnick P. A., Smith D., Tabb D. L., Tegeler T. J., Variyath A. M., Vega-Montoto L. J., Wahlander A., Waldemarson S., Wang M., Whiteaker J. R., Zhao L., Anderson N. L., Fisher S. J., Liebler D. C., Paulovich A. G., Regnier F. E., Tempst P., and Can S. A. (2009) Multi-site assessment of the precision and reproducibility of multiple reaction monitoring-based measurements of proteins in plasma. Nat. Biotechnol. 27, 633-641

43. Keshishian, H., Addona T., Burgess M., Mani D. R., Shi X., Kuhn E., Sabatine M. S., Gersten R. E., and Can S. A. (2009) Quantification of cardiovascular biomarkers in patient plasma by targeted mass spectrometry and stable isotope dilution. Mol. Cell Proteomics 8, 2339-2349

44. Kuhn, E., Addona T., Keshishian H., Burgess M., Mani D. R., Lee R. T., Sabatine M. S., Gersten R. E., and Can S. A. (2009) Developing multiplexed assays for troponin I and interleukin-33 in plasma by peptide immunoaffinity enrichment and targeted mass spectrometry. Clin. Chem. 55, 1108-1117

45. Green, J. M. (996) A practical guide to analytical method validation. Anal. Chem. 68, A305-A309

46. Kuzyk, M. A., Smith D., Yang J., Cross T. J., Jackson A. M., Hardie D. B., Anderson N. L., and Borchers C. H. (2009) Multiple reaction monitoring-based, multiplexed, absolute quantitation of 45 proteins in human plasma. Mol. Cell Proteomics 8, 1860-1877

47. Nelson, D. E., Ihekwaba A. E. C., Elliott M., Johnson J. R., Gibney C. A., Foreman B. E., Nelson G., See V., Horton C. A., Spiller D. G., Edwards S. W., McDowell H. P., Unitt J. F., Sullivan E., Grimley R., Benson N., Broomhead D., Kell D. B., and White M. R. H. (2004) Oscillations in NF-{kappa}B Signaling Control the Dynamics of Gene Expression. Science 306, 704-708

48. Wurster, S. E., Maher L. J. (2008) Selection and characterization of anti-NF-+|B p65 RNA aptamers. RNA 14, 1037-1047

49. Bassett, S. E., Fennewald S. M., King D. J., Li X., Herzog N. K., Shope R., Aronson J. F., Luxon B. A., and Gorenstein D. G. (2004) Combinatorial Selection and Edited Combinatorial Selection of Phosphorothioate Aptamers Targeting Human Nuclear Factor-kB RelA/p50 and RelA/RelA. Biochemistry 43, 9105-9115

50. Chen, Y. Q., Ghosh S., and Ghosh G. (2011) A novel DNA recognition mode by the NF-kappa B p65 homodimer. Nature Structural Biology 5, 67-73

51. Huang, D. B., Vu D., Cassiday L. A., Zimmerman J. M., Maher L. J., and Ghosh G. (2003) Crystal structure of NF-kB (p50)2 complexed to a high-affinity RNA aptamer. Proceedings of the National Academy of Sciences of the United States of America 100, 9268-9273

52. Jacobs, M. D., Harrison S. C. (1998) Structure of an I[kappa]B[alpha]/NF-[kappa]B Complex. Cell 95, 749-758

53. Berezovski, M. V., Lechmann M., Musheev M. U., Mak T. W., and Krylov S. N. (2008) Aptamer-facilitated biomarker discovery (AptaBiD). J. Am. Chem. Soc. 130, 9137-9143

54. Hoffmann, A., Levchenko A., Scott M. L., and Baltimore D. (2002) The IkappaB-NF-kappaB signaling module: Temporal control and selective gene activation. Science 298, 1241-1245

55. Lipniacki, T., Paszek P., Brasier A. R., Luxon B., and Kimmel M. (2004) Mathematical model of NF-kappaB regulatory module. J Theor Biol 228, 195-215

56. Kallita, M., Sargayesan K., Tian B., Pauluccia A., Najm H., Brasier A. R., and DeBusschere B. (2010) Bayesian Inference of NF-B Signaling Pathway Parameters based on Single Cell Dynamic Images. PLoS Computational Biology under review.

57. Barnes, P. J., and Karin, M. 1997. Nuclear factor-kappaB: a pivotal transcription factor in chronic inflammatory diseases. [Review] [53 refs]. N Engl J Med 336:1066-1071.

58. Dror, R., Lederman, M., Umezawa, K., Barak, V., Pe'er, J., and Chowers, I. 2010. Characterizing the Involvement of the Nuclear Factor-kappa B (NF+|B) Transcription Factor in Uveal Melanoma. Investigative Ophthalmology & Visual Science 51:1811-1816.

59. Wang, D., and Richmond, A. 2001. Nuclear factor-kB activatin by the CXC chemokine melanoma growth-stimulatory activity/growth-regulated protein involves the MEKK1/p38 mitogen activated protein kinase pathway. J. Biol. Chem. 276:3650-3659.

60. Sweeney, C., Li, L., Shanmugam, R., Bhat-Nakshatri, P., Jayaprakasan, V., Baldridge, L. A., Gardner, T., Smith, M., Nakshatri, H., and Cheng, L. 2004. Nuclear Factor-+|B Is Constitutively Activated in Prostate Cancer In vitro and Is Overexpressed in Prostatic Intraepithelial Neoplasia and Adenocarcinoma of the Prostate. Clinical Cancer Research 10:5501-5507.

61. Brasier, A. R., Recinos, A. I., and Eledrisi, M. S. 2005. Mechanisms for vascular inflammation as a cardiovascular risk factor. In Principles of Molecular Cardiology. M. Runge, and Patterson, C., editors. Humana Press.

62. Brasier, A. R., Recinos, A. I., and Eledrisi, M. S. 2002. Vascular inflammation and the renin angiotensin system. Arteriosclerosis, Thrombosis & Vascular Biology 22:1257-1266.

63. Brasier, A. R. 2010. The Nuclear Factor-kB Interleukin-6 Signaling Pathway Mediating Vascular Inflammation. Cardiovasc Res 86:211-218.

64. Brand, K., Page, S., Rogler, G., Bartsch, A., Brandl, R., Kneuchel, R., Page, M., Kaltschmidt, C., Baeuerle, P. A., and Neumeier, D. 1996. Activated transcription factor nuclear factor-kB is present in the atherosclerotic lesion. J Clin Invest 97:1715-1722.

65. Greten, F. R., Eckmann, L., Greten, T. F., Park, J. M., Li, Z. W., Egan, L. J., Kagnoff, M. F., and Karin, M. 2004. IKK[beta] Links Inflammation and Tumorigenesis in a Mouse Model of Colitis-Associated Cancer. Cell 118:285-296.

What is claimed is:

1. A composition comprising:
   an isolated single-stranded oligonucleotide for binding to an activated Nuclear Factor-κB (NF-κB)/RelA complex, wherein the oligonucleotide comprises SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or the binding-specific variable regions thereof.

2. The composition of claim 1, wherein the oligonucleotide comprises SEQ ID NO: 21.

3. A testing kit for quantification of a level of activated RelA in a sample comprising:
   a first vial comprising an isolated single-stranded oligonucleotide that binds specifically to a RelA comprising the aptamers of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or the binding-specific variable regions thereof;
   a second optional vial comprising reagents to detect the binding of the oligonucleotide and RelA; and
   an instruction booklet comprising step-by-step directions for the usage of the kit.

4. The testing kit of claim 3, wherein the single-stranded oligonucleotide is immobilized onto beads, suspended in a liquid medium, or immobilized on a probe.

5. The testing kit of claim 3, wherein the sample is a cellular extract, a growth medium, a body fluid or any combinations thereof.

6. The testing kit of claim 3, wherein the single-stranded oligonucleotide comprises the binding-specific variable regions of SEQ ID NO: 9.

7. The testing kit of claim 3, wherein the reagents are adapted for in vivo imaging.

8. The testing kit of claim 3, wherein the single-stranded oligonucleotide may be conjugated to one or more effectors, wherein the effectors are selected from the group consisting of radionuclides, gold, magnetic nanoparticles, fluorescent labels, quantum dots, and gadolinium.

9. A single-stranded oligonucleotide for binding to an activated Nuclear Factor-κB (NF-κB)/RelA complex, wherein the single-stranded oligonucleotide is selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or binding-specific variable regions thereof.

10. A composition comprising: a single-stranded oligonucleotide aptamer comprising at least 97%, 94% or 91% homology to at least one of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or the binding-specific variable regions thereof, wherein the aptamer binds an activated Nuclear Factor-κB (NF-κB)/RelA complex.

11. The composition of claim 10, wherein the single-stranded oligonucleotide aptamer consists of at least one of SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, or binding-specific variable regions thereof.

12. The composition of claim 10, wherein the single-stranded oligonucleotide aptamer consists of SEQ ID NO: 21.

* * * * *

SEQUENCE LISTING

<160> NUMBER OF SEQ ID NOS: 21

<210> SEQ ID NO 1
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 1
ggtaaccttg agtcacgaat tcaa                                              24

<210> SEQ ID NO 2
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 2
cagaagctgt aagttgggta cctt                                              24

<210> SEQ ID NO 3
<211> LENGTH: 15
<212> TYPE: DNA
<213> ORGANISM: artificial sequence
<220> FEATURE:
<223> OTHER INFORMATION: synthetic oligonucleotide

<400> SEQUENCE: 3
atacgggaat tcccg                                                        15

<210> SEQ ID NO 4
<211> LENGTH: 17
<212> TYPE: DNA
<213> ORGANISM: artificial sequence
<220> FEATURE:
<223> OTHER INFORMATION: synthetic oligonucleotide

<400> SEQUENCE: 4
actaggaatt tccagtg                                                      17

<210> SEQ ID NO 5
<211> LENGTH: 17
<212> TYPE: DNA
<213> ORGANISM: artificial sequence
<220> FEATURE:
<223> OTHER INFORMATION: synthetic oligonucleotide

<400> SEQUENCE: 5
cactggaaat tcctagt                                                      17

<210> SEQ ID NO 6
<211> LENGTH: 14
<212> TYPE: PRT
<213> ORGANISM: artificial sequence
<220> FEATURE:
<223> OTHER INFORMATION: synthetic peptide

<400> SEQUENCE: 6

Thr Pro Pro Tyr Ala Asp Pro Ser Leu Gln Ala Pro Val Arg
1               5                   10

```
<210> SEQ ID NO 7
<211> LENGTH: 8
<212> TYPE: PRT
<213> ORGANISM: artificial sequence
<220> FEATURE:
<223> OTHER INFORMATION: synthetic peptide

<400> SEQUENCE: 7

Leu Glu Pro Gln Glu Val Pro Arg
1               5

<210> SEQ ID NO 8
<211> LENGTH: 9
<212> TYPE: PRT
<213> ORGANISM: artificial sequence
<220> FEATURE:
<223> OTHER INFORMATION: synthetic peptide

<400> SEQUENCE: 8

Ala Val Phe Pro Ser Ile Val Gly Arg
1               5

<210> SEQ ID NO 9
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 9
gggtaacctt gagtcacgaa ttcaagcggg acaggagaaa cacggcatgt cagcgaaggt      60
acccaactta cagcttctgg                                                  80

<210> SEQ ID NO 10
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 10
gggtaacctt gagtcacgaa ttcaatagcg ggccaggatg gaaggtatgg cagcgaaggt      60
acccaactta cagcttctgg                                                  80

<210> SEQ ID NO 11
<211> LENGTH: 79
<212> TYPE: DNA
<213> ORGANISM: artificial sequence
<220> FEATURE:
<223> OTHER INFORMATION: synthetic oligonucleotide

<400> SEQUENCE: 11
ctttggtcag cctctaatgg ctcgtgggac agtgtgtgtt cagtcaaacg tggctggctc      60
tccaagaatc cccgtagtt                                                   79

<210> SEQ ID NO 12
<211> LENGTH: 80
<212> TYPE: DNA
<213> ORGANISM: artificial sequence
<220> FEATURE:
<223> OTHER INFORMATION: synthetic oligonucleotide
```

<400> SEQUENCE: 12
ctttggtcag cctctaatgg ctcgtggcag gaacgggcct tagcttggca ttgggtggct    60
ctccaagaat ccccgtagtt                                                80

<210> SEQ ID NO 13
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 13
ctttggtcag cctctaatgg ctcgtgggac aggaggtacg gaatgtcagc gaacgtggct    60
ctccaagaat ccccgtagtt                                                80

<210> SEQ ID NO 14
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 14
gggtaacctt gagtcacgaa ttcaagcagt tcccactgac cttaaattct gcaccaaggt    60
acccaactta cagcttctgg                                                80

<210> SEQ ID NO 15
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 15
gggtaacctt gagtcacgaa ttcaaccact cctattcaca ctatcccctt tcccgaaggt    60
acccaactta cagcttctgg                                                80

<210> SEQ ID NO 16
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 16
gggtaacctt gagtcacgaa ttcaaccaca aaatcgtgcc gttcaatatc tgaccaaggt    60
acccaactta cagcttctgg                                                80

<210> SEQ ID NO 17
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 17
ctttggtcag cctctaatgg ctcgtgggga gcacacgcat tggtaccgtc tggtatggct    60
ctccaagaat ccccgtagtt                                                80

```
<210> SEQ ID NO 18
<211> LENGTH: 10
<212> TYPE: DNA
<213> ORGANISM: artificial sequence
<220> FEATURE:
<223> OTHER INFORMATION: synthetic oligonucleotide

<400> SEQUENCE: 18
gggactttcc                                                                   10

<210> SEQ ID NO 19
<211> LENGTH: 20
<212> TYPE: PRT
<213> ORGANISM: artificial sequence
<220> FEATURE:
<223> OTHER INFORMATION: synthetic peptide

<400> SEQUENCE: 19

Val Phe Arg Thr Pro Pro Tyr Ala Asp Pro Ser Leu Gln Ala Pro Val
 1               5                  10                  15

Arg Val Ser Met
            20

<210> SEQ ID NO 20
<211> LENGTH: 80
<212> TYPE: DNA
<213> ORGANISM: artificial sequence
<220> FEATURE:
<223> OTHER INFORMATION: synthetic oligonucleotide

<400> SEQUENCE: 20
gggtaacctt gagtcacgaa ttcaaacctc ttcactcccc tcactactgc ttataaaggt           60
acccaactta cagcttctgg                                                       80

<210> SEQ ID NO 21
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 21
gcgggacagg agaaacacgg catgtcagcg                                            30
```